United States Patent [19]
Goldsteen et al.

[11] Patent Number: 5,976,178
[45] Date of Patent: Nov. 2, 1999

[54] MEDICAL GRAFTING METHODS

[75] Inventors: David S. Goldsteen, Minneapolis; Thomas J. Bachinski, Lakeville; Rudy Mazzocchi, Dellwood; Daniel J. Sullivan, Medina, all of Minn.

[73] Assignee: Vascular Science Inc., Minneapolis, Minn.

[21] Appl. No.: 08/745,618

[22] Filed: Nov. 7, 1996

[51] Int. Cl.⁶ .............................. A61F 2/06; A61M 29/00; A61B 17/00

[52] U.S. Cl. ................................ 623/1; 623/12; 623/66; 623/11; 606/151; 606/153; 606/191; 606/194; 604/49; 604/158; 604/163; 604/272; 128/898

[58] Field of Search ................................... 623/1, 11, 12; 600/8; 128/898; 604/49–54, 158, 159, 163, 164, 272; 606/108, 113, 185, 194–195

[56] References Cited

U.S. PATENT DOCUMENTS

| | | | |
|---|---|---|---|
| 3,903,892 | 9/1975 | Komiya | 128/303.15 |
| 4,214,587 | 7/1980 | Sakura, Jr. | 128/334 R |
| 4,418,693 | 12/1983 | LeVeen et al. | 128/303 |
| 4,459,252 | 7/1984 | MacGregor | 264/46.9 |
| 4,503,569 | 3/1985 | Dotter | 3/1.4 |
| 4,592,754 | 6/1986 | Gupte et al. | 623/1 |
| 4,605,406 | 8/1986 | Cahalan et al. | 623/1 |
| 4,617,932 | 10/1986 | Kornberg | 128/334 R |
| 4,629,458 | 12/1986 | Pinchuk | 623/1 |
| 4,632,842 | 12/1986 | Karwoski et al. | 427/2 |
| 4,651,733 | 3/1987 | Mobin-Uddin | 128/303 R |
| 4,665,918 | 5/1987 | Garza et al. | 128/343 |
| 4,705,517 | 11/1987 | DiPisa, Jr. | 623/1 |
| 4,718,907 | 1/1988 | Karwoski et al. | 623/12 |
| 4,733,665 | 3/1988 | Palmaz | 128/343 |
| 4,738,740 | 4/1988 | Pinchuk et al. | 156/167 |
| 4,743,252 | 5/1988 | Martin, Jr. et al. | 623/1 |
| 4,748,984 | 6/1988 | Patel | 128/658 |
| 4,787,899 | 11/1988 | Lazarus | 623/1 |
| 4,795,458 | 1/1989 | Regan | 623/1 |
| 4,798,606 | 1/1989 | Pinchuk | 623/1 |
| 4,892,539 | 1/1990 | Koch | 623/1 |
| 4,969,890 | 11/1990 | Sugita et al. | 606/192 |
| 5,035,702 | 7/1991 | Taheri | 606/153 |

(List continued on next page.)

FOREIGN PATENT DOCUMENTS

| | | | |
|---|---|---|---|
| 670239 | 1/1994 | Australia | A61F 2/06 |
| 539237 | 4/1993 | European Pat. Off. | A61F 2/06 |
| 637454 A1 | 2/1995 | European Pat. Off. | A61M 25/10 |
| 680734 A2 | 11/1995 | European Pat. Off. | A61F 2/06 |
| 684022 A2 | 11/1995 | European Pat. Off. | A61F 2/06 |
| 0 712 614 A1 | 5/1996 | European Pat. Off. | A61F 2/06 |
| 0 732 087 A1 | 9/1996 | European Pat. Off. | A61F 2/06 |
| 0 737 453 A2 | 10/1996 | European Pat. Off. | A61F 2/06 |
| 44 04 806 C1 | 2/1995 | Germany | A61B 17/22 |
| 2 269 104 | 2/1994 | United Kingdom | A61F 2/06 |
| WO 93/00868 | 1/1993 | WIPO | A61F 2/06 |
| WO 94/06372 | 3/1994 | WIPO | A61F 2/04 |
| WO 95/17127 | 6/1995 | WIPO | A61B 17/11 |
| WO 96/01591 | 1/1996 | WIPO | A61B 17/22 |
| WO 96/01599 | 1/1996 | WIPO | A61F 2/06 |
| WO 96/18361 | 6/1996 | WIPO | A61F 2/06 |
| WO 96/22745 | 8/1996 | WIPO | A61F 2/06 |

(List continued on next page.)

*Primary Examiner*—David J. Isabella
*Assistant Examiner*—Choon P. Koh
*Attorney, Agent, or Firm*—Fish & Neave; Robert R. Jackson

[57] ABSTRACT

Methods and apparatus for delivering and installing a new length of tubing between two sections of a patient's existing body organ tubing and at least partly outside of that existing structure. For example, the new length of tubing may be for the purpose of providing the patient with a coronary bypass. The new tubing may be an artificial graft, a natural graft (harvested elsewhere from the patient), or both. The new tubing is delivered to and installed at the operative site primarily by working through the patient's existing tubular body organ structure. This avoids the need for any significant surgery on the patient. The artificial grafts may have shapes other than tubular. Certain procedural and apparatus aspects of the invention have uses other than in connection with grafting in general or tubular grafting in particular.

40 Claims, 24 Drawing Sheets

U.S. PATENT DOCUMENTS

| | | | |
|---|---|---|---|
| 5,037,377 | 8/1991 | Alonso | 600/36 |
| 5,061,245 | 10/1991 | Waldvogel | 604/170 |
| 5,061,275 | 10/1991 | Wallsten et al. | 623/1 |
| 5,084,065 | 1/1992 | Weldon et al. | 623/1 |
| 5,104,399 | 4/1992 | Lazarus | 623/1 |
| 5,116,360 | 5/1992 | Pinchuk et al. | 623/1 |
| 5,122,154 | 6/1992 | Rhodes | 606/198 |
| 5,147,370 | 9/1992 | McNamara et al. | 606/108 |
| 5,163,951 | 11/1992 | Pinchuk et al. | 623/1 |
| 5,171,233 | 12/1992 | Amplatz et al. | 604/281 |
| 5,201,901 | 4/1993 | Harada et al. | 606/198 |
| 5,209,731 | 5/1993 | Sterman et al. | 604/97 |
| 5,211,658 | 5/1993 | Clouse | 623/1 |
| 5,211,683 | 5/1993 | Maginot | 128/898 |
| 5,226,429 | 7/1993 | Kuzmak | 128/898 |
| 5,256,150 | 10/1993 | Quiachon et al. | 604/171 |
| 5,275,622 | 1/1994 | Lazarus et al. | 623/1 |
| 5,287,861 | 2/1994 | Wilk | 128/898 |
| 5,297,564 | 3/1994 | Love | 128/898 |
| 5,304,220 | 4/1994 | Maginot | 623/1 |
| 5,306,240 | 4/1994 | Berry | 604/51 |
| 5,316,023 | 5/1994 | Palmaz et al. | 128/898 |
| 5,334,217 | 8/1994 | Das | 606/213 |
| 5,354,309 | 10/1994 | Schnepp-Pesch et al. | 606/198 |
| 5,360,443 | 11/1994 | Barone et al. | 623/1 |
| 5,366,504 | 11/1994 | Andersen et al. | 623/11 |
| 5,387,235 | 2/1995 | Chuter | 623/1 |
| 5,395,349 | 3/1995 | Quiachon et al. | 604/248 |
| 5,397,345 | 3/1995 | Lazarus | 623/1 |
| 5,409,019 | 4/1995 | Wilk | 128/898 |
| 5,419,324 | 5/1995 | Dillow | 128/653.1 |
| 5,425,765 | 6/1995 | Tiefenbrun et al. | 623/12 |
| 5,429,144 | 7/1995 | Wilk | 128/898 |
| 5,433,727 | 7/1995 | Sideris | 606/213 |
| 5,437,288 | 8/1995 | Schwartz et al. | 128/772 |
| 5,443,497 | 8/1995 | Venbrux | 623/1 |
| 5,443,499 | 8/1995 | Schmitt | 623/1 |
| 5,452,733 | 9/1995 | Sterman et al. | 128/898 |
| 5,456,712 | 10/1995 | Maginot | 623/1 |
| 5,480,423 | 1/1996 | Ravenscroft et al. | 623/1 |
| 5,484,418 | 1/1996 | Quiachon et al. | 604/167 |
| 5,489,295 | 2/1996 | Piplani et al. | 623/1 |
| 5,496,364 | 3/1996 | Schmitt | 623/1 |
| 5,496,365 | 3/1996 | Sgro | 623/1 |
| 5,507,769 | 4/1996 | Marin et al. | 606/198 |
| 5,509,931 | 4/1996 | Schmitt | 623/1 |
| 5,522,834 | 6/1996 | Fonger et al. | 606/194 |
| 5,522,880 | 6/1996 | Barone et al. | 623/1 |
| 5,542,944 | 8/1996 | Bhatta | 606/33 |
| 5,545,214 | 8/1996 | Stevens | 623/2 |
| 5,549,663 | 8/1996 | Cottone, Jr. | 623/1 |
| 5,554,152 | 9/1996 | Aita et al. | 606/7 |
| 5,562,725 | 10/1996 | Schmitt et al. | 623/1 |
| 5,571,172 | 11/1996 | Chin | 623/1 |
| 5,584,875 | 12/1996 | Duhamel et al. | 623/1 |
| 5,628,788 | 5/1997 | Pinchuk | 623/1 |
| 5,632,772 | 5/1997 | Alcime et al. | 623/1 |
| 5,653,747 | 8/1997 | Dereume | 623/1 |
| 5,676,670 | 10/1997 | Kim | 606/108 |
| 5,695,504 | 12/1997 | Gifford, III et al. | 606/153 |
| 5,830,222 | 11/1998 | Makower | 606/159 |

FOREIGN PATENT DOCUMENTS

| | | | |
|---|---|---|---|
| WO 96/25897 | 8/1996 | WIPO | A61F 2/06 |
| WO 97/13463 | 4/1997 | WIPO | A61B 17/00 |
| WO 97/13471 | 4/1997 | WIPO | A61B 19/00 |
| WO 97/27893 | 8/1997 | WIPO | A61M 19/00 |
| WO 97/27897 | 8/1997 | WIPO | A61M 29/00 |
| WO 97/27898 | 8/1997 | WIPO | A61M 29/00 |
| WO 98/08456 | 3/1998 | WIPO | A61B 19/00 |
| WO 98/16161 | 4/1998 | WIPO | A61B 17/36 |

MEDICAL GRAFTING METHODS

BACKGROUND OF THE INVENTION

This invention relates to grafts for use in the repair, replacement, or supplement of a medical patient's natural body organ structures or tissues. The invention also relates to methods for making graft structures. The invention further relates to methods and apparatus for delivering a graft to an operative site in a patient, and for installing the graft at that site. Some aspects of the invention may have other uses such as for viewing the interior of a patient, providing access to the interior of a patient for other procedures, etc. An example of the possible uses of the invention is a minimally invasive cardiac bypass procedure. This example will be considered in detail, but it will be understood that various aspects of the invention have many other possible uses.

Several procedures are known for revascularizing the human heart in order to treat a patient with one or more occluded coronary arteries. The earliest of these procedures to be developed involves exposing the heart by means of a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel such as a length of the patient's saphenous (leg) vein is harvested for use as a graft. The graft is used to create a new, uninterrupted channel between a blood source, such as the aorta, and the occluded coronary artery or arteries downstream from the arterial occlusion or occlusions.

A variation of the above procedure involves relocating a mammary artery of the patient to a coronary artery.

Although the above-described sternotomy procedures are increasingly successful, the high degree of invasiveness of these procedures and the requirement of these procedures for general anesthesia are significant disadvantages. Indeed, these disadvantages preclude use of s3ternotomy procedures on many patients.

More recently, less invasive procedures have been developed for revascularizing the heart. An example of these procedures is known as thoracostomy, which involves surgical creation of ports in the patient's chest to obtain access to the thoracic cavity. Specially designed instruments are inserted through the port, to allow the surgeon to revascularize the heart withou the trauma of a midline sternotomy. Drugs may be administered to the patient to slow the heart during the procedure. Some thoracostomy procedures involve relocating a mammary artery to a coronary artery to provide a bypass around an occlusion in the coronary artery.

Thoracostomy bypass procedures are less traumatic than sternotomy bypass procedures, but they are still too traumatic for some patients. Also, the number of required bypasses may exceed the number of mammary arteries, thereby rendering thoracostomy procedures inadequate to fully treat many patients.

Another technique for revascularizing the human heart involves gaining access to the thoracic cavity by making incisions between the patient's ribs. This procedure is known as thoracotomy. It is also substantially less traumatic than midline sternotomy, but it is still too traumatic for some patients.

In view of the foregoing, it is an object of this invention to provide less traumatic methods and apparatus for revascularizing a patient.

It is another object of the invention to provide minimally invasive methods and apparatus for repairing, replacing, or supplementing the blood vessels or other body organ tubing or tissues of a patient.

It is still another object of the invention to provide improved graft structures for use in the repair, replacement, or supplementing of natural body organ structures or tissues, and to provide methods for making such graft structures.

It is yet another object of the invention to provide improved methods and apparatus for transporting or delivering and installing graft structures for use in the repair, replacement, or supplementing of natural body organ structures or tissues of a patient.

SUMMARY OF THE INVENTION

These and other objects of the invention are accomplished in accordance with the principles of the invention by providing methods and apparatus for substantially non-surgically installing a new length of tubing in a patient between two sections of the patient's existing body organ tubing, the new length of tubing being delivered to the operative site by passing along existing tubing, but installed at the operative site so that it is at least partly outside the existing tubing. (As used herein, references to a patient's existing body organ tubing or the like include both natural and previously installed graft tubing (whether natural, artificial, or both). A previous installation of graft tubing may have occurred in a previous procedure or earlier in a current and on-going procedure. References to a length of tubing also include plural lengths of tubing.) At one end of the operative site, the new length of tubing is caused to extend out through an opening made in the existing tubing. The outwardly extending end portion of the new tubing is guided to the other end of the operative site. At that other end another opening is made in the existing tubing and the extending end portion of the new tubing is attached to the existing tubing via that opening. The other end portion of the new tubing (remote from the extending portion) is similarly attached to the existing tubing at the first-described opening. The new tubing installation is now complete, and the apparatus used to make the installation can be withdrawn from the patient.

In the most preferred embodiment, all or substantially all necessary apparatus is inserted into the patient via the patient's existing body organ tubing. In addition, all or substantially all apparatus functions at the operative site are remotely controlled by the physician (a term used herein to also include supporting technicians) from outside the patient's body.

Preferred apparatus in accordance with the invention includes a first elongated instrument for extending through the patient's existing body organ tubing to a first end of the operative site, and a second elongated instrument for similarly extending through the patient's existing tubing to a second end of the operative site. Each instrument includes a structure capable of penetrating the existing tubing at the associated end of the operative site. In addition, these structures are capable of interengaging with one another outside he existing tubing to provide a substantially continuous structural path from outside the patient, along the patient's existing tubing, and then outside that tubing from one end to the other of the operative site. This structure is used to guide the new length of tubing into the patient and into position at the operative site.

At least one of the elongated instruments preferably includes mechanisms for fastening each end portion of the new length of tubing to the adjacent existing body organ tubing. For example, these mechanisms may activate fasteners on or associated with the new tubing.

The new tubing may be artificial graft tubing. Alternatively, the new tubing may be natural body organ tubing (e.g., tubing harvested from another location in the patient's body). As still another alternative, the new tubing may be a combination of artificial and natural tubing (e.g., natural tubing disposed substantially concentrically inside artificial tubing).

A preferred form of artificial tubing includes a tube frame of a first highly elastic material (such as nitinol) covered with a second highly elastic material (such as silicone rubber) to substantially fill in the apertures in the frame. This combination produces an artificial graft that is distensible like natural body organ tubing such as a natural artery. The covering on the frame is preferably made porous to a predetermined degree to improve its bio-utility in this context. A preferred method of providing such porosity is to make the covering from an elastic material that is mixed with particles of a material that can be removed (e.g., by vaporization) after the covering has been applied to the mesh. When the particles are removed, voids are left in the covering that give it the desired porosity.

The artificial grafts of this invention may be coated (in the case of tubular grafts, on the inside and/or outside) to still further enhance their bio-utility. Examples of suitable coatings are medicated coatings, hydrophylic coatings, smoothing coatings, collagen coatings, human cell seeding coatings, etc. The above-described preferred porosity of the graft covering helps the graft to retain these coatings. Additional advantages of the artificial grafts of this invention are their elasticity and distensibility (mentioned above), their ability to be deployed through tubes of smaller diameter (after which they automatically return to their full diameter), the possibility of making them modular, their ability to accept natural body organ tubing concentrically inside themselves, their ability to support development of an endothelial layer, their compatibility with MRI procedures, their ability to be made fluoroscopically visible, etc.

Although grafts in the form of tubing are described above, certain aspects of the invention are equally applicable to other graft procedures and to grafts having other shapes.

Further features of the invention, its nature and various advantages will be more apparent from the accompanying drawings and the following detailed description of the preferred embodiments.

BRIEF DESCRIPTION OF THE DRAWINGS

FIG. 7f is a simplified elevational view of an alternative embodiment of still another component shown in FIG. 7a.

FIG. 7g is a simplified elevational view of an alternative embodiment of yet another component shown in FIG. 7a.

FIG. 15b is a view similar to FIG. 15a showing more of the structure of which FIG. 15a is a part.

DETAILED DESCRIPTION OF THE PREFERRED EMBODIMENTS

Because the present invention has a number of different applications, each of which may warrant some modifications of such parameters as instrument size and shape, it is believed best to describe certain aspects of the invention with reference to relatively generic schematic drawings. To keep the discussion from becoming too abstract, however, and as an aid to better comprehension and appreciation of the invention, references will frequently be made to specific uses of the invention. Most often these references will be to use of the invention to provide a bypass around an occlusion or obstruction (generically referred to as a narrowing) in a patient's coronary artery, and in particular a bypass from the aorta to a point along the coronary artery which is downstream from the coronary artery narrowing. It is emphasized again, however, that this is only one of many possible applications of the invention.

Figure 1:
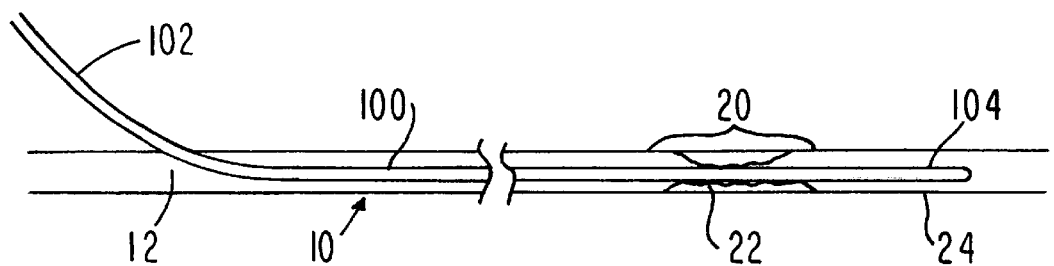
FIG. 1 is a simplified longitudinal sectional view showing a portion of an illustrative procedure and related apparatus in accordance with this invention.

Assuming that the invention is to be used to provide a bypass from the aorta around a coronary artery narrowing, the procedure may begin by inserting an elongated instrument into the patient's circulatory system so that a distal portion of the instrument extends through the coronary artery narrowing to the vicinity of the point along the artery at which it is desired to make the bypass connection. This is illustrated by FIG. 1 which shows elongated instrument 100 entering the patient's circulatory system 10 at a remote location 12 and passing coaxially along vessels in the circulatory system until its distal end portion 104 passes through narrowing 22 in coronary artery 20 and reaches the downstream portion 24 of the artery to which it is desired to make a bypass connection. For example, the entry location 12 of irnstrument 100 may be a femoral (leg) artery of the patient, a brachial artery of the patient, or any other suitable entry point. It will be appreciated, however, that entry point 12 is typically remote from the location at which the bypass is to be provided, and that control of instrument 100 throughout its use is from the proximal portion 102 that is outside the patient at all times.

Figure 2:
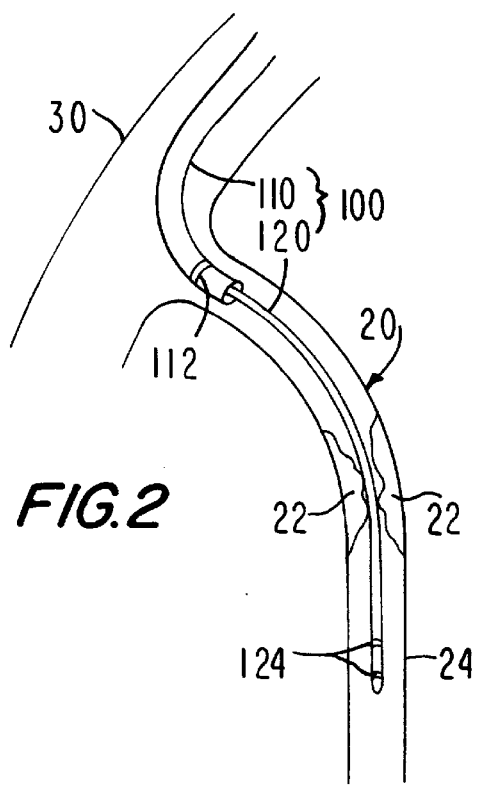
FIG. 2 is a simplified longitudinal sectional view showing a portion of a more particular illustrative procedure and related apparatus in accordance with the invention.

For the illustrative procedure being discussed, FIG. 2 shows a preferred embodiment of instrument 100 in more detail. As shown in FIG. 2, instrument 100 may include a catheter tube 110 which is inserted (from location 12 in FIG. 1) via the patient's aorta 30 to the ostium of coronary artery 20. Another tubular structure 120 is then extended from the distal end of catheter 110, through narrowing 22 to location 24.

Figure 3:
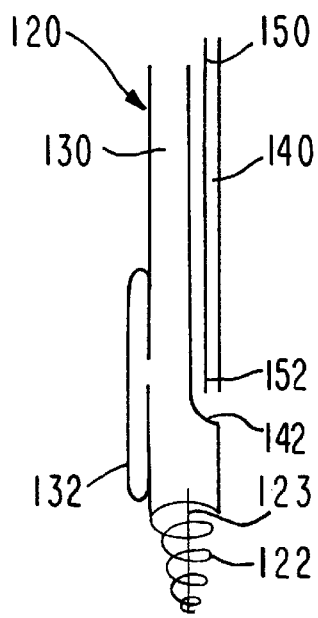
FIG. 3 is a simplified longitudinal sectional view showing an illustrative embodiment of a portion of the FIG. 2 apparatus in more detail.
Figure 4:
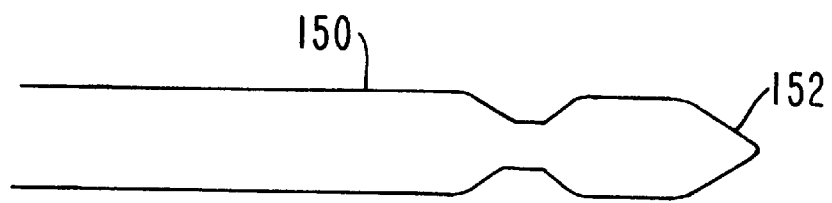
FIG. 4 is a simplified elevational view showing an illustrative embodiment of a portion of the FIG. 3 apparatus in still more detail.

An illustrative construction of tubular structure 120 is shown in more detail in FIG. 3. There it will be seen that structure 120 may have two lumens 130 and 140. Near the distal end of structure 120, lumen 130 communicates with the interior of an inflatable balloon 132 on one side of structure 120, while lumen 140 opens out to the opposite side of structure 120. Lumen 140 contains a longitudinal structure 150 which may be a stylet wire with a sharpened distal tip 152 (see FIG. 4). (Although FIG. 4 shows indentations behind tip 152, those indentations could be eliminated if desired.) Structure 120 may be provided with a distal spring tip 122 to help guide the distal end of structure 120 along coronary artery 20 and through narrowing 22. A safety ribbon 123 (e.g., of the same material as tip 122) may be connected at its proximal end to the distal end of member 120 and at its distal end to the distal end of tip 122 to improve the performance of tip 122 and to help prevent separation of any portion of tip 122 from structure 120 in the event of damage to tip 122. Structure 120 may have radiologic (e.g., radio-opaque or fluoroscopically viewable) markers 124 at suitable locations to help the physician place the structure where desired in the patient's body. Catheter 110 may also have radiologic markers 112 for similar use. Balloon 132 is initially deflated. Longitudinal structure 150 is initially retracted within lumen 140. However, the distal portion of lumen 140 is shaped (as indicated at 142 in FIG. 2) to help guide the distal tip 152 of structure 150 out to the side of structure 120 when structure 150 is pushed distally relative to structure 120. This is discussed in more detail below. As earlier description suggests, each of components 110, 120, and 150 is separately controllable from outside the patient, generally indicated as region 102 in FIG. 1.

Figure 3A:
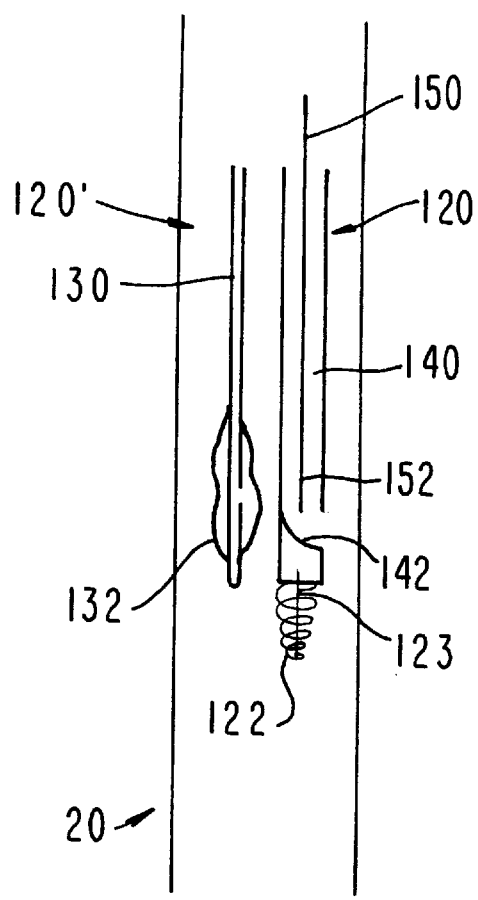
FIG. 3a is a view similar to FIG. 3 showing an alternative illustrative embodiment of the FIG. 3 apparatus.

As an alternative to providing balloon 132 as an integral part of one structure 120, balloon 132 may be provided on another longitudinal structure 120' (FIG. 3a) which is substantially parallel to the remaining components described above for structure 120. Structure 120' may be substantially separate from structure 120, or it may be attached to structure 120.

Figure 5:
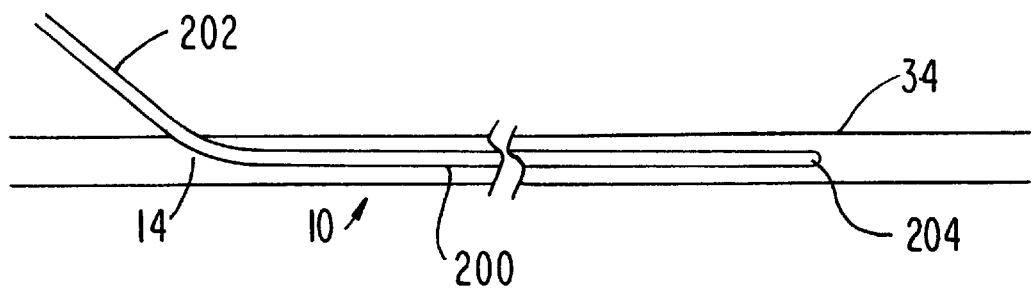
FIG. 5 is a simplified longitudinal sectional view showing another portion of an illustrative procedure and related apparatus in accordance with this invention.
Figure 6:
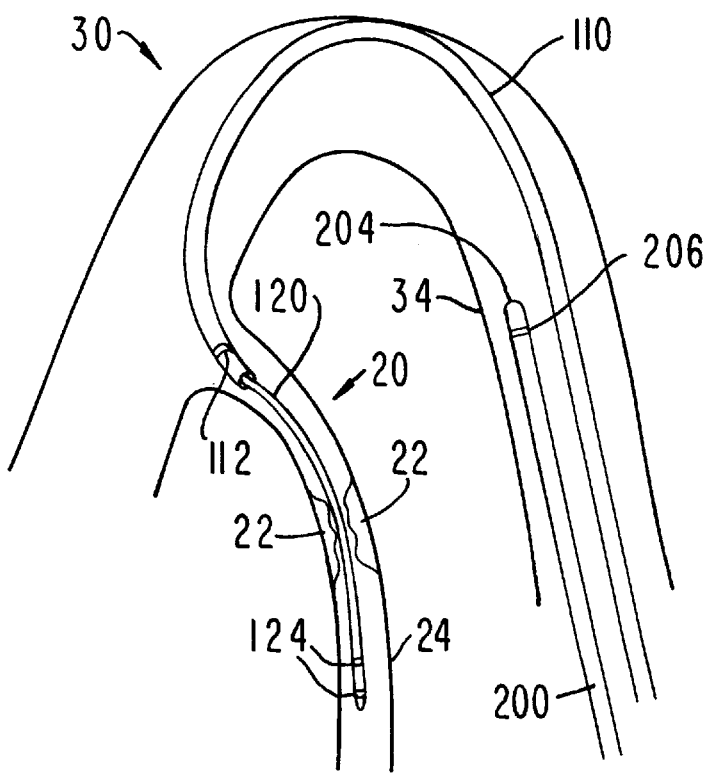
FIG. 6 is a view similar to FIG. 2 showing a later stage in the illustrative procedure depicted in part by FIG. 2, together with related apparatus, all in accordance with this invention.

After instrument 100 is positioned as shown in FIGS. 1 and 2, a second elongated instrument 200 is similarly introduced into the patient's circulatory system 10 as shown generally in FIG. 5. For example, instrument 200 may enter the patient (at 14) via a femoral artery, a brachial artery, or any other suitable location, which again is typically remote from the bypass site. If one femoral artery is used to receive instrument 100, the other femoral artery may be used to receive instrument 200. Or the same femoral artery may be used to receive both instruments. Or any other combination of entry points may be used for the two instruments. Instrument 200 is inserted until its distal end is adjacent to the point 34 in the circulatory system which it is desired to connect to point 24 via a bypass. This is illustrated in a more specific example in FIG. 6 where the distal end of instrument 200 is shown at location 34 in aorta 30. The particular location 34 chosen in FIG. 6 is only illustrative, and any other location along aorta 30 may be selected instead. Radiologic markers 206 may be provided on the distal portion of instrument 200 to help the physician position the instrument where desired. Note that FIG. 6 shows portions of instruments 100 and 200 side by side in aorta 30.

Figure 7A:
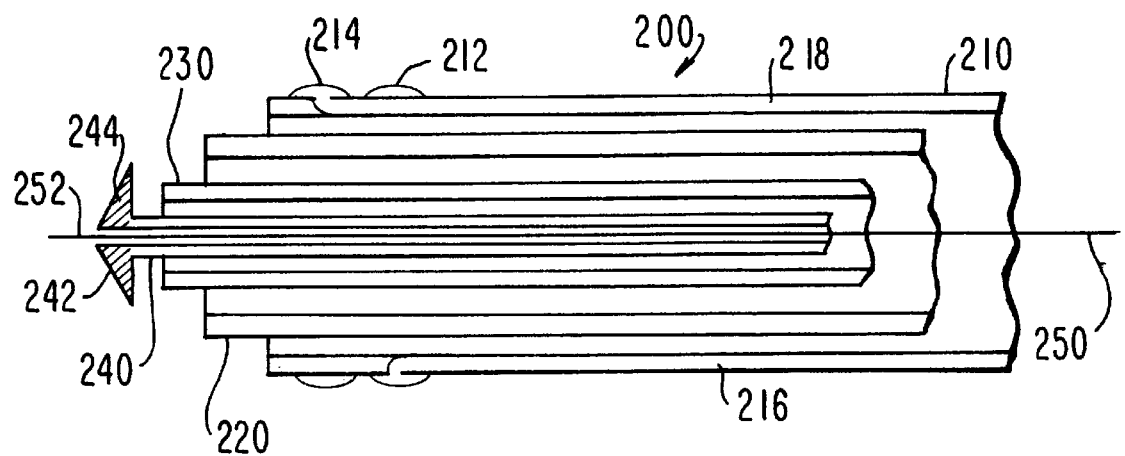
FIG. 7a is a simplified longitudinal sectional view of an illustrative embodiment of a portion of the FIG. 6 apparatus in more detail.

An illustrative construction of instrument 200 is shown in more detail in FIG. 7a. This FIG. shows the distal portions of elements 220, 230, 240, and 250 telescoped out from one another and from the distal end of outer member 210 for greater clarity. It will be understood, however, that all of these elements are initially inside of one another and inside outer member 210. Indeed, member 210 may be initially positioned in the patient without any or all of elements 220, 230, 240, and 250 inside, and these elements may then be inserted into member 210. Moreover, the number of members like 220, 230, etc., may be more or less than the number shown in FIG. 7a, depending on the requirements of a particular procedure.

Outer member 210 may be a catheter-type member. The distal portion of catheter 210 may carry two axially spaced annular balloons 212 and 214. Proximal balloon 212 is inflatable and deflatable via inflation lumen 216 in catheter 210. Distal balloon 214 is inflatable and deflatable via inflation lumen 218 in catheter 210. Lumens 216 and 218 are separate from once another so that balloons 212 and 214 can be separately controlled. Balloons 212 and 214 are shown substantially deflated in FIG. 7a. The distal end of catheter 210 may be tapered as shown at 211 in FIG. 7c to facilitate passage of catheter 210 through an aperture in aorta 30 as will be described below.

Coaxially inside catheter 210 is tubular sheath member 220. Sheath 220 is longitudinally movable relative to catheter 210. The distal portion of sheath 220 may be tapered as shown at 222 in FIG. 7d, and/or externally threaded as shown at 224 in FIG. 7e. Either or both of features 222 and 224 may be provided to facilitate passage of sheath 220 through an aperture in aorta 30 as will be described below. If threads 224 are provided, then sheath 220 is rotatable (either alone or with other components) about the longitudinal axis of instrument 200 in order to enable threads 224 to engage the tissue of the aorta wall and help pull sheath 220 through the aorta wall.

Coaxially inside sheath member 220 is power steering tube 230. Tube 230 is longitudinally movable relative to sheath 220. Tube 230 may also be rotatable (about the central longitudinal axis of instrument 200) relative to sheath 220, and the distal end of tube 230 may be threaded on the outside (as shown at 232 in FIG. 7f) for reasons similar to those for which threading 224 may be provided on sheath 220. Tube 230 is preferably controllable from its proximal portion (outside the patient) to deflect laterally by a desired amount to help steer, push, or twist instrument 200 to the desired location in the patient.

Coaxially inside tube 230 is tube 240. Tube 240 is longitudinally movable relative to tube 230, and may be metal (e.g., stainless steel) hypotube, for example. Screw head 242 is mounted on the distal end of tube 240 and is threaded (as indicated at 244) on its distal conical surface. Tube 240 is rotatable (about the central longitudinal axis of instrument 200, either alone or with other elements) in order rotate head 242 and thereby use threads 244 in engagement with the tissue of the aorta wall to help pull head 242 through that wall as will be more fully described below. Because tube 240 is hollow, it can he used for passage of fluid or pressure into or out of the patient.

Figure 7B:
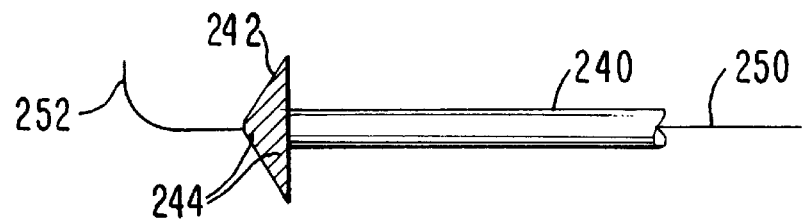
FIG. 7b is a simplified elevational view of a portion of the FIG. 7a apparatus, but with the depicted elements in a different physical relationship to one another.
Figure 7C:
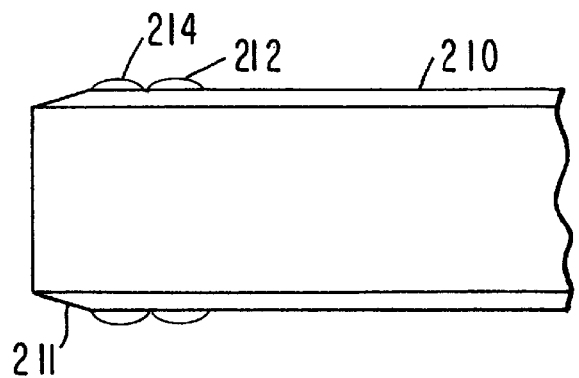
FIG. 7c is a simplified longitudinal sectional view of an alternative embodiment of one component of the FIG. 7a apparatus.
Figure 7D:
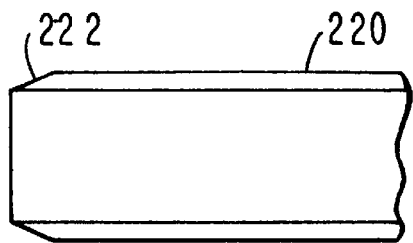
FIG. 7d is a simplified longitudinal sectional view of an alternative embodiment of another component of the FIG. 7a apparatus.
Figure 7E:
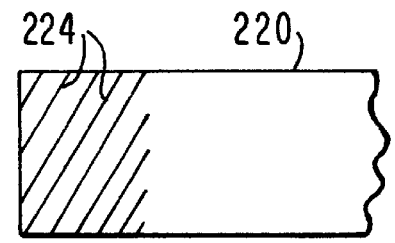
FIG. 7e is a simplified elevational view of another alternative embodiment of the component shown in FIG. 7d.
Figure 7F:
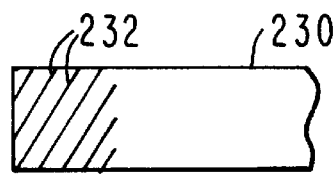
Figure 7G:
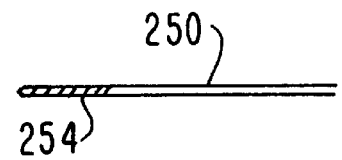

Coaxially inside tube 240 is longitudinal structure 250. Longitudinal structure 250 is longitudinally movable relative to tube 240. Structure 250 may also be rotatable (about its longitudinal axis) relative to tube 240 and/or other elements. Structure 250 may be a wire with a distal end portion 252 that is resiliently biased to deflect laterally to one side. Wire portion 252 is kept relatively straight when it is inside tube 240 as shown in FIG. 7a. But when wire portion 252 is pushed axially out the distal end of tube 240, it curves to one side as shown in FIG. 7b. As an alternative or addition to the above-described resilient lateral deflection, the distal portion of structure 250 may be threaded as shown at 254 in FIG. 7g to help structure 250 thread its way through the wall of aorta 30.

All of components 210, 220, 230, 240, and 250 are controlled from outside the patient's body (i.e., from region 202 in FIG. 5).

When the distal portion of catheter 210 is at the desired location 34, proximal balloon 212 is inflated. Even when inflated, proximal balloon 212 is not large enough to block aorta 30.

After proximal balloon 212 has been inflated, wire 250 is pushed distally so that its distal portion emerges from the distal end of tube 240 and penetrates the wall of aorta 30 at location 34. This anchors the distal portion of instrument 200 to the aorta wall at the desired location. Because of its operation to thus anchor instrument 200, wire 250 is sometimes referred to as an anchor wire. The rotatability of wire 250, as well as its resilient lateral deflection (FIG. 7b) and/or threads 254 (FIG. 7g), may be used to help get the distal end of the wire to the desired location 34 and firmly into the aorta wall at that location in order to achieve the desired anchoring of instrument 200.

When instrument 200 is sufficiently anchored by wire 250, tubes 230 and 240 are moved in the distal direction relative to wire 250 so that screw head 242 begins to follow wire 250 into and through the aorta wall. During this motion, at least tube 240 is rotated about its longitudinal axis so that threads 244 help to pull head 242 into and through the aorta wall. The distal portion of tube 230 follows head 242 through the aorta wall. If provided, threads 232 and rotation of tube 230 may facilitate transfer of the aorta wall tissue from head 242 to tube 230.

When tube 230 is through the aorta wall, sheath 220 is moved distally relative to tube 230 so that a distal portion of sheath 220 follows tube 230 through the aorta wall. If provided, the distal taper 222 and/or threads 224 and rotation of sheath 220 help the distal portion of sheath 220 through the aorta wall. Then catheter 210 is advanced distally relative to sheath 220 so that a distal portion of catheter 210 follows sheath 220 through the aorta wall. Again, the distal taper 211 of catheter 210 (if provided) helps the distal portion of the catheter through the aorta wall. Inflated proximal balloon 212 prevents more than just the portion of catheter 210 that is distal of balloon 212 front passing through the aorta wall.

It should be mentioned that each time another, larger one of elements 240, 230, 220, and 210 is pushed through the aorta wall, the previously extended elements can be and preferably are either held stationary or pulled back proximally to prevent them from damaging body tissues outside the aorta.

Figure 8:
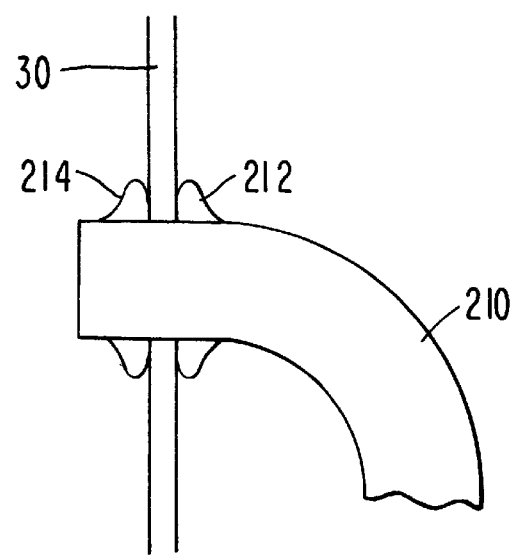
FIG. 8 is a simplified longitudinal sectional view similar to a portion of FIG. 6 showing a still later stage in the illustrative procedure depicted in part by FIG. 6.
Figure 8A:
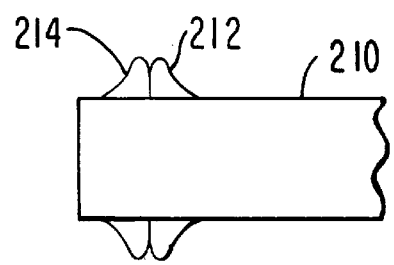
FIG. 8a is a simplified sectional view of the apparatus shown in FIG. 8 without the associated tissue structure being present.

When the distal portion of catheter 210 is through the aorta wall, distal balloon 214, which is now outside the aorta, is also inflated. The axial spacing between balloons 212 and 214 is preferably small enough so that the aorta wall is clamped between these two balloons as shown in FIG. 8. For example, if balloons 212 and 214 were inflated without the presence of the aorta wall, their appearance might be as shown in FIG. 8a. The close spacing of balloons 212 and 214, as well as their resilient bias toward one another, helps to anchor catheter 210 through the aorta wall and also to seal the aorta wall around the catheter. Balloons 212 and 214 may be inflated by liquid or gas, and they may be specially coated to help improve the seal between catheter 210 and the aorta wall.

After the condition of catheter 210 shown in FIG. 8 has been reached, all of components 220, 230, 240, and 250 can be withdrawn from the patient by pulling them out of catheter 210 in the proximal direction.

Figure 9:
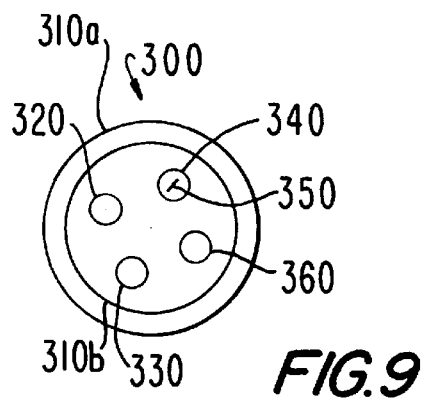
FIG. 9 is a simplified cross sectional view of an illustrative embodiment of further illustrative apparatus in accordance with this invention.

The next step in the illustrative procedure being described is to insert an elongated, steerable, endoscopic snare 300 lengthwise into catheter 210. A simplified cross sectional view of an illustrative steerable endoscopic snare is shown in FIG. 9. As shown in that FIG., snare 300 includes one or more sheath structures such as 310a and 310b that are operable by the physician to steer the snare by curvilinearly deflecting it laterally by a desired, variable amount. Within sheaths 310 are such other components as (1) a fiber optic bundle 320 for conveying light from outside the patient to the distal end of snare 300 in order to provide illumination beyond the distal end of the snare, (2) another fiber optic bundle 330 for conveying an image from beyond the distal end of the snare back to optical and/or video equipment outside the patient and usable by the physician to see what is beyond the distal end of the snare, and (3) a snare sheath 340 with the actual snare instrument 350 inside of it. Additional lumens such as 360 may be provided for such purposes as introducing fluid that may help to clear the distal ends of fiber optic bundles 320 and 330, for introducing fluid for irrigating and/or medicating the patient, for suctioning fluid from the patient, etc. It may not be necessary to provide a separate snare sheath 340, but rather element 340 may merely be a lumen through the general structure 300 for snare instrument 350.

Figure 10:
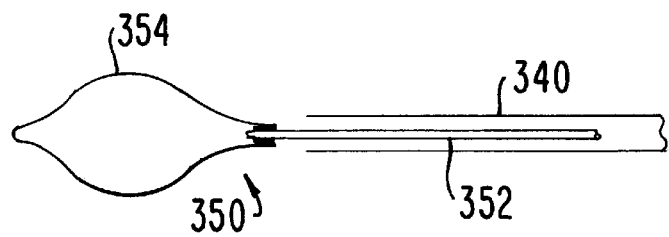
FIG. 10 is a simplified longitudinal sectional view of an illustrative embodiment of a portion of the FIG. 9 apparatus.

An illustrative embodiment of the distal portion of snare instrument 350 is shown in FIG. 10. In this embodiment instrument 350 includes a wire 352 with a snare loop 354 (also of wire) at its distal end. Loop 354 is closed when it is inside snare sheath or lumen 340. Loop 354 opens resiliently to the shape shown in FIG. 10 when it extends distally beyond the distal end of sheath or lumen 340.

Figure 10A:
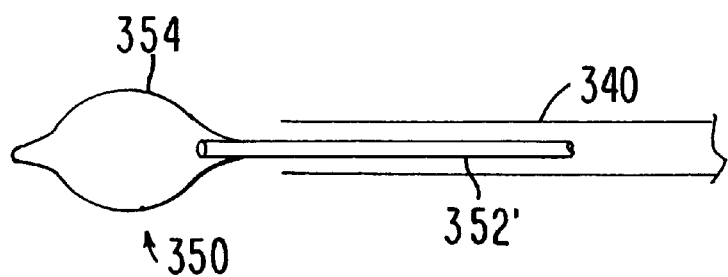
FIG. 10a is a view similar to FIG. 10 showing a possible alternative construction of the FIG. 10 apparatus.

In the alternative embodiment of instrument 350 shown in FIG. 10a, snare loop 354 is mounted on the distal end of a fiber optic bundle 352'. Fiber optic bundle 352' may perform the functions described above for bundle 320 or bundle 330, thereby integrating those functions into instrument portion 350.

Figure 10B:
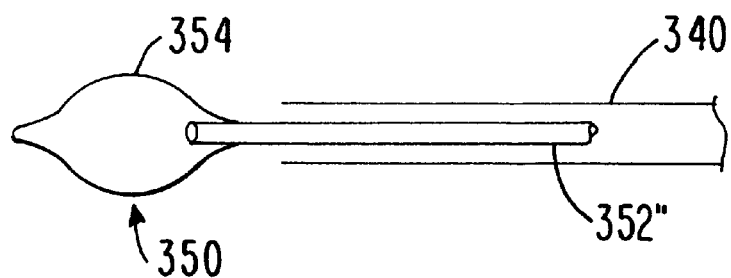
FIG. 10b is another view similar to FIG. 10 showing another possible alternative construction of the FIG. 10 apparatus.

In the further alternative embodiment of instrument 350 shown in FIG. 10b, snare loop 354 is mounted on the distal end of a tube 352", which can be used to deliver other types of instrumentation to the vicinity of snare loop 354. For example, tube 352" may be metal (e.g., stainless steel) hypotube, and the other instrumentation delivered via that tube may be a tissue cutter for use in cooperation with snare loop 354 to perform a biopsy.

Figure 10C:
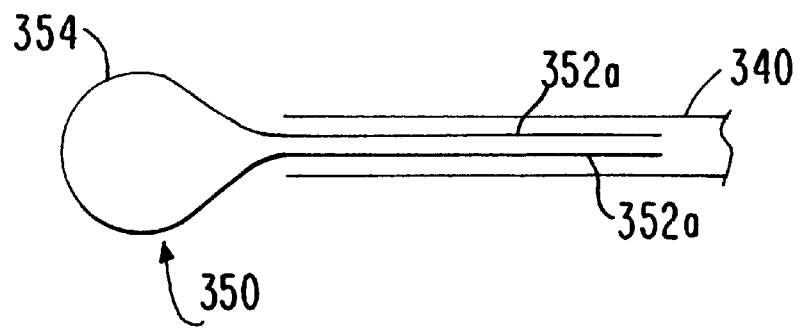
FIG. 10c is another view similar to FIG. 10 showing still another possible alternative construction of the FIG. 10 apparatus.

In the still further alternative embodiment shown in FIG. 10c, snare loop 354 is part of one continuous length of wire 352a. A possible advantage of the embodiment shown in FIG. 10c is that it permits snare loop 354 to be variable in size, determined by how much of wire 352a is extended from the distal end of lumen 340.

Figure 11:
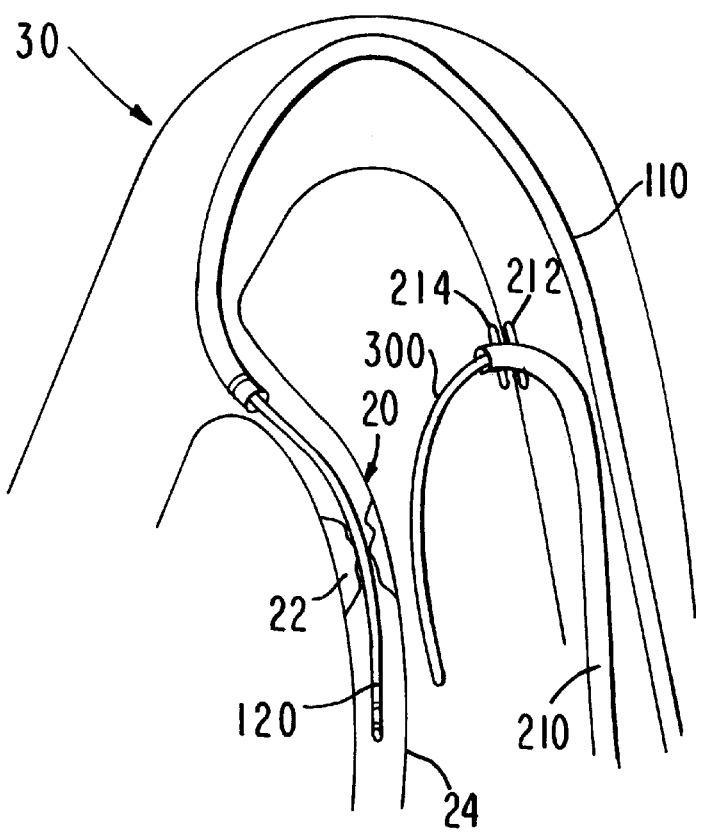
FIG. 11 is a view similar to FIG. 6 showing an even later stage in the illustrative procedure depicted in part by FIG. 8, together with related apparatus, all in accordance with this invention.

As shown in FIG. 11, the distal portion of steerable endoscopic snare 300 is extended distally beyond the distal end of catheter 210 and steered by the physician until it is adjacent to the exterior of coronary artery portion 24.

Figure 12:
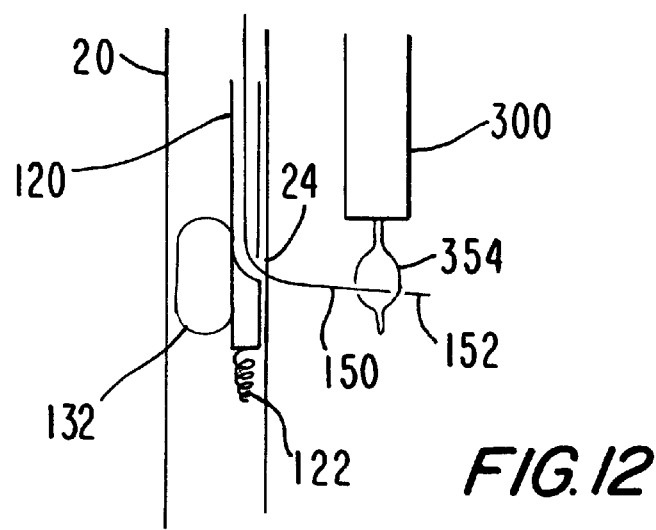
FIG. 12 is a view similar to a portion of FIG. 11, but in somewhat more detail, showing a still later stage in the illustrative procedure depicted in part by FIG. 11.

The next step in the illustrative procedure being described is preferably to deploy snare loop 354 by extending it distally from the distal end of structure 300 as shown in FIG. 12. Alternatively, this step could be performed somewhat later.

The next step (also shown in FIG. 12) is to inflate balloon 132 to push tube 120 against the opposite side wall of coronary artery 20 at location 24. Then stylet wire 150 is moved in the distal direction as shown in FIG. 12 so that its distal tip 152 passes through the wall of the coronary artery. As was mentioned earlier, the distal end of the stylet wire lumen in tube 120 is shaped to help guide stylet wire 150 through the coronary artery wall. After stylet wire 150 is through the coronary artery wall, balloon 132 can be deflated. Balloon 132 may be a perfusion balloon which allows continued blood flow along artery 20 even while the balloon is inflated.

Figure 12A:
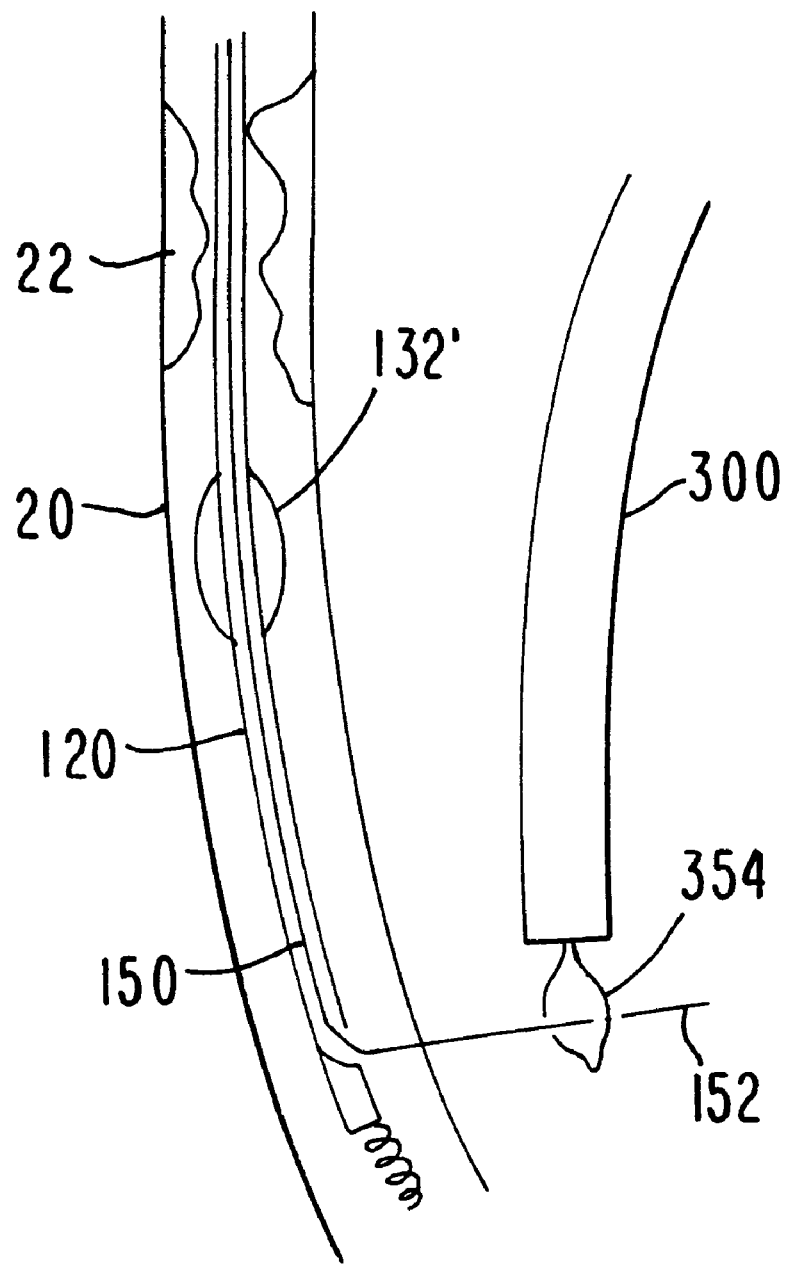
FIG. 12a is a view similar to FIG. 12 showing a possible alternative construction of the FIG. 12 apparatus.

It may not be necessary to have a balloon 132 directly opposite the outlet for wire 150. For example, FIG. 12a shows an alternative embodiment in which a perfusion balloon 132' is provided on tube 120 proximally of the outlet for wire 150. Balloon 132' is inflated when it is desired to stabilize the location of tube 120 in coronary artery 20 (e.g., while the distal portion of wire 150 is being pushed out through the coronary artery wall). Another possibility is for a balloon like 132' to be near the distal end of a balloon catheter from which tube 120 extends distally. Still another possibility may be to omit balloons like 132 and 132' entirely. If a balloon 132 or 132' is provided, it may not be necessary for it to be a perfusion balloon.

When the distal portion of stylet wire 150 is outside coronary artery 20, the next step is to ensure that the distal portion of the wire passes through snare loop 354 as shown in FIG. 12 or FIG. 12a. This may be facilitated by continued use of the visual observation and steering capabilities of snare 300. An especially preferred technique is to deploy snare loop 354 so that it is next to coronary artery section 24. Then when stylet wire 150 emerges from the coronary artery at 24, it immediately passes through snare loop 354 with no further manipulation being required.

Once wire 150 is through snare loop 354, snare sheath or lumen 340 is moved distally relative to the snare loop. This causes snare loop 354 to close down on wire 150. Snare sheath or lumen 340 also tends to trap the distal portion of wire 150 and to fold that wire portion back on itself inside sheath or lumen 340 as shown in FIG. 13.

Figure 13:
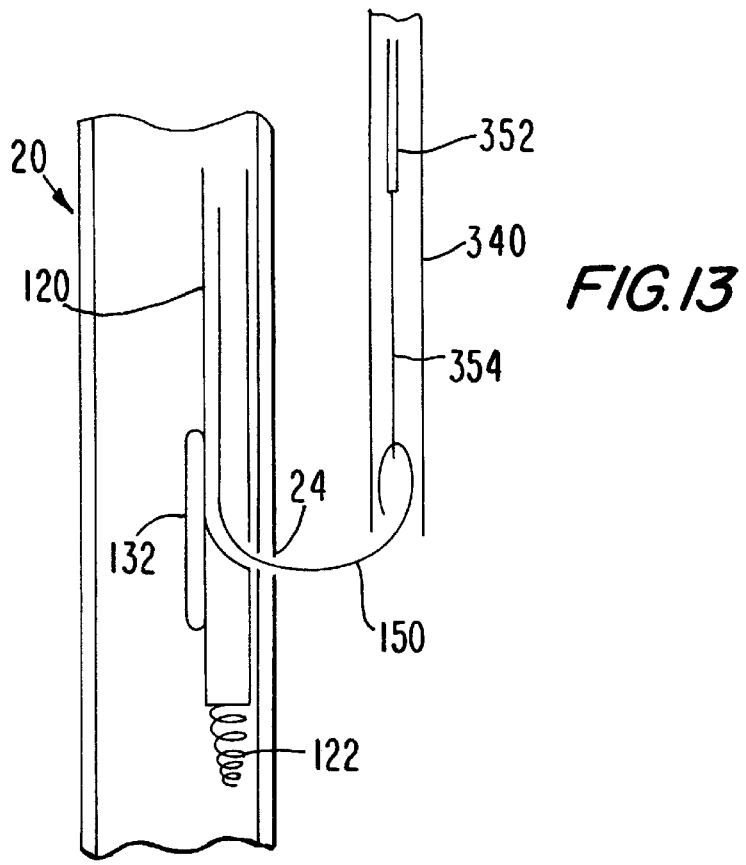
FIG. 13 is a view similar to FIG. 12 showing an even later stage in the illustrative procedure depicted in part by FIG. 12.

When the condition shown in FIG. 13 is achieved, longitudinal structures 150 and 350 are securely interencgaged inside snare sheath or lumen 340. The next step is to pull wire 352 in the proximal direction all the way out of the patient at location 202 (FIG. 5). Because of the interengagement between wires 150 and 352, withdrawing wire 352 pulls as much additional wire 150 into the patient from external location 102 (FIG. 1). When wire 352 has been completely removed from the patient, there is then one continuous wire 150 from outside the patient at 102, through the patient, to outside the patient at 202. Wire 150 can now be moved in either longitudinal direction through the patient. This wire or another wire could be used to help pull various apparatus into the patient via the tube or tubes through which the wire passes.

Figure 14:
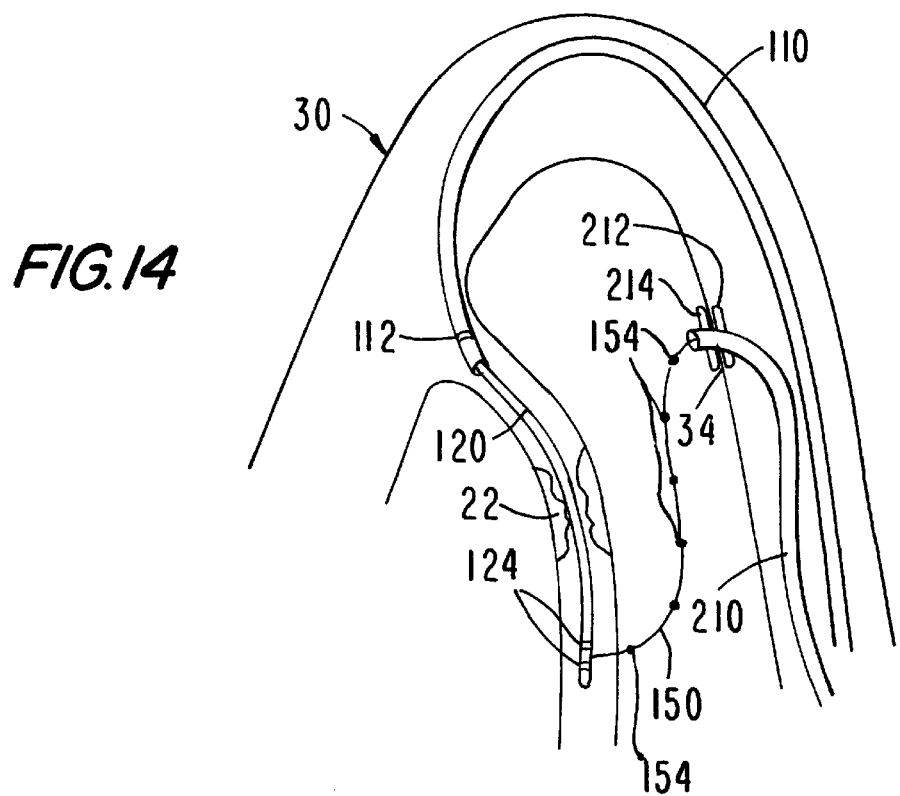
FIG. 14 is a view similar to FIG. 11 showing a still later stage in the illustrative procedure depicted in part by FIG. 13.

After one continuous wire 150 has been established through the patient as described above, steerable endoscopic snare 300 may be withdrawn from the patient by pulling it proximally out of catheter 210. The condition of the apparatus inside the patient is now as shown in FIG. 14. Note that the resence of fixed outlets for the wire from the distal ortion of tube 120 and the distal end of catheter 210 prevents wire 150 from cutting tissues 20 and 30 when the wire is pulled in either longitudinal direction. The portion of whre 150 extending through the interior of the patient between elements 120 and 210 may have radiologic markers 154 equally spaced along its length. These can be viewed radiologically by the physician to determine the distance between regions 24 and 34 via wire 150. This helps the physician select the correct length of graft needed between regions 24 and 34.

The next phase of the illustrative procedure being described is to install a new length of tubing between regions 24 and 34. The new length of tubing may be either an artificial graft, natural body organ tubing harvested from the patient's body, or a combination of artificial and natural tubing (e.g., natural tubing coaxially inside artificial tubing). In the following discussion it is assumed that the new tubing is to be natural tubing (e.g., a length of the patient's saphenous vein that has been harvested for this purpose) inside an artificial conduit. When such a combination of natural and artificial conduits is used, both conduits can be delivered and installed simultaneously, Dr the outer artificial conduit can be delivered and installed first, and then the inner natural conduit can be delivered and installed. The following discussion initially assumes that the latter technique is employed.

Figure 15:
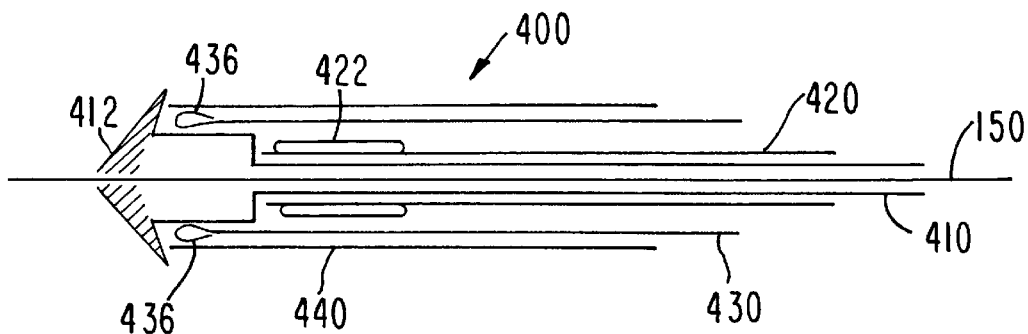
FIG. 15 is a simplified longitudinal sectional view of an illustrative embodiment of a portion of still further illustrative apparatus in accordance with this invention.

In accordance with the above-stated assumptions, the next step in the procedure is to use catheter 210 and wire 150 to deliver an artificial conduit so that it extends between regions 24 and 34. The distal portion of an illustrative assembly 400 for doing this is shown in FIG. 15. (Several alternative constructions of this portion of the apparatus are shown in later FIGS. and described below.)

As shown in FIG. 15 assembly 400 includes a threaded, conical, distal tip 412 mounted on a tubular member 410 (e.g., metal hypotube) through which wire 150 can freely pass. Additional details regarding various possible constructions of tip 412 are provided later with reference to FIGS. 15a–15g, but it should be mentioned here that in this embodiment tip 412 is selectively collapsible to facilitate its withdrawal from the patient after it has served its purpose. Another tubular member 420 is disposed concentrically around tubular member 410. An inflatable balloon 422 is mounted on the distal end of tubular member 420. Tubular member 420 includes an axially extending lumen (not shown in FIS. 15) for use in selectively inflating and deflating balloon 422. Balloon 422 is shown deflated in FIG. 15.

Figure 16:
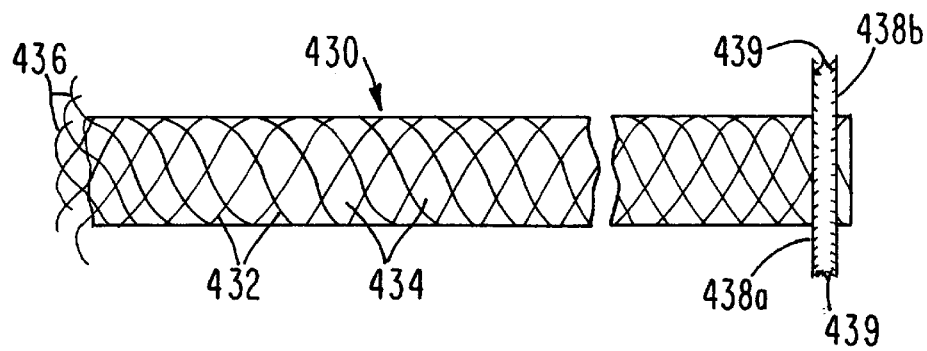
FIG. 16 is a simplified elevational view of an illustrative embodiment of one component of the FIG. 15 apparatus.

Coaxially around tubular member 420 is an artificial graft conduit 430. An illustrative embodiment of a suitable conduit 430 is shown in FIG. 16 and inclades a tube formed of a frame 432 of a first highly elastic material (such as nitinol) with a covering 434 of a second highly elastic material (e.g., a rubber-like material such as silicone) substantially filling the apertures in the frame. Additional information regarding this possible embodiment of conduit 430 and Dther artificial graft structures in accordance with the invention is provided in later portions of this specification. Here it will suffice to say that this structure is extremely elastic, flexible, pliable, and resilient. For example, it can be stretched to a small fraction of its original diameter, and it thereafter returns by itself to its original size and shape without damage or permanent deformation of any kind. In addition, this structure is distensible so that it may pulsate very much like natural circulatory system tubing in response to pressure waves in the blood flow. This helps keep the conduit open, especially if it is used by itself as the final graft conduit. At its distal end, extensions of frame 432 are flared out to form resilient hooks or barbs 436, the purpose of which will become apparent as the description proceeds. Near the proximal end of conduit 430 two axially spaced resilient flaps 438a and 438b with barbs 439 are provided. The purpose and operation of elements 438 and 439 will also become apparent as the description proceeds.

In assembly 400 (see again FIG. 15, and also FIG. 17), barbs 436 and flaps 438 are compressed radially inwardly and confined within conduit delivery tube 440, which c,oaxially surrounds conduit 430. Indeed, conduit 430 may be somewhat circumferentially compressed by tube 440.

Figure 17:
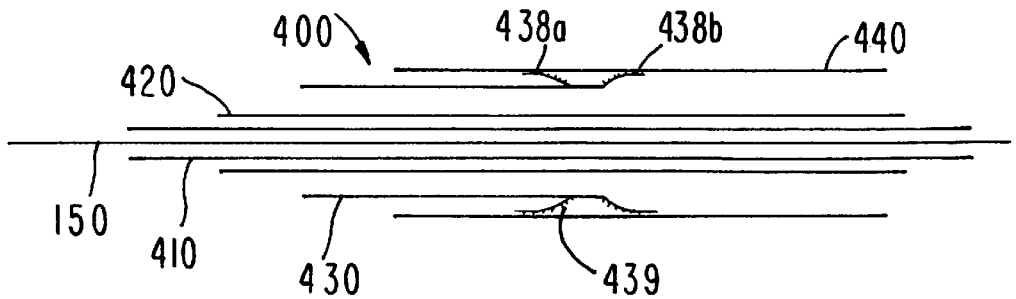
FIG. 17 is a simplified longitudinal sectional view of an illustrative embodiment of another portion of the FIG. 15 apparatus.

The portion of assembly 440 at which the proximal end of conduit 430 is located is shown in FIG. 17. There it will be seen how flaps 438 are confined within conduit delivery tube 440. FIG. 17 also shows how tubes 410, 420, and 440 extend proximally (to the right as viewed in FIG. 17) from the proximal end of conduit 430 so that the physician can remotely control the distal portion of assembly 400 from outside the patient.

Figure 18:
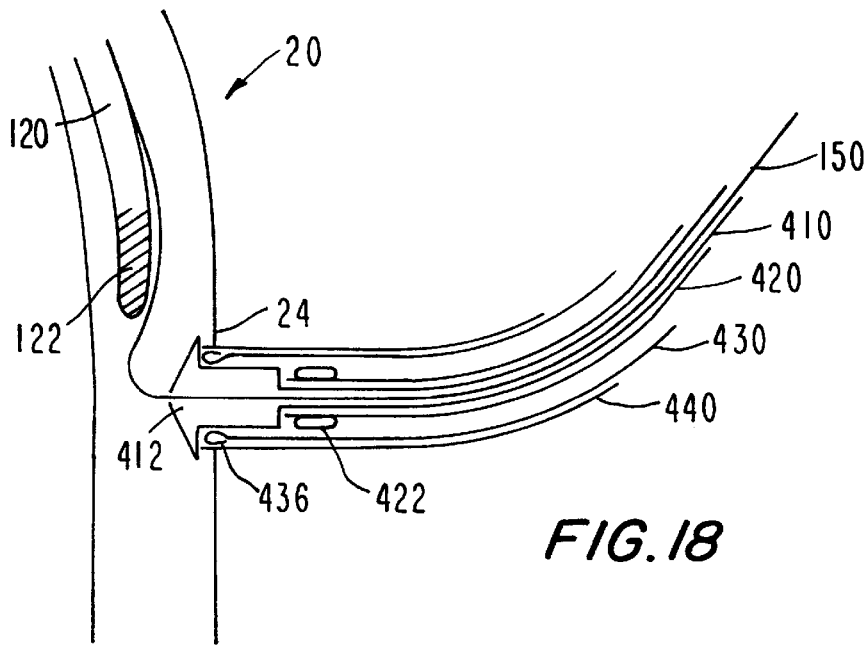
FIG. 18 is a view similar to a portion of FIG. 14 showing an even later stage in the illustrative procedure depicted in part by FIG. 14.

To install artificial graft conduit 430 in the patient between regions 24 and 34, assembly 400 is fed into the patient along wire 150 through catheter 210. When tip 412 reaches coronary artery portion 24, tip 412 is threaded into and through the coronary artery wall by rotating tube 410 and therefore tip 412. (Tube 120 may be pulled back slightly at this time to make sure that it does not obstruct tip 412.) The passage of tip 412 through the coronary artery wall opens up the aperture in that wall. After tip 412 passes through thIe artery wall, that wall seals itself against the outside of the distal portion of conduit delivery tube 440D as shown in FIG. 18.

Figure 19:
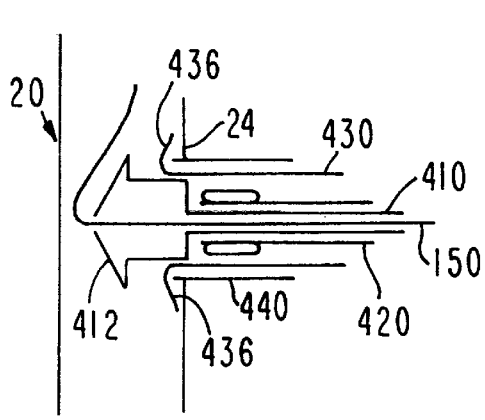
FIG. 19 is a view similar to FIG. 18 showing a still later stage in the FIG. 18 procedure.

The next step is to push tube 410 and tip 412 distally relative to delivery tube 440, which is held stationary. Conduit 430 is initially moved distally with components 410 and 412. This may be done by inflating balloon 422 so that it engages conduit 430, and then moving tube 420 distally with components 410 and 412. Distal motion of conduit 430 moves barbs 436 beyond the distal end of delivery tube 440, thereby allowing the barbs to spring out inside coronary artery 20 as shown in FIG. 19. This prevents the distal end of conduit 430 from being pulled proximally out of the coronary artery. If balloon 422 was inflated during this phase of the procedure, it may be deflated before beginning the next phase.

Figure 20:
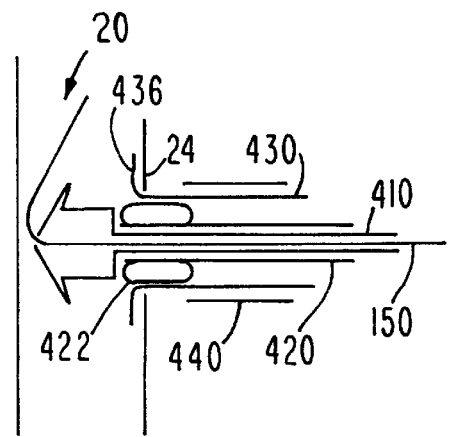
FIG. 20 is a view similar to FIG. 19 showing an even later stage in the FIG. 19 procedure.

The next step is to pull delivery tube 440 back slightly so that it is withdrawn from coronary artery 20. Then tube 420 is moved distally so that balloon 422 is radially inside the annulus of barbs 436. Balloon 442 is then inflated to ensure that barbs 436 are firmly set in coronary artery 20. Conditions are now as shown in FIG. 20. Cross sections of balloon 422 may be L-shaped when inflated (one leg of the L extending parallel to the longitudinal axis of conduit 430, and the other leg of the L extending radially outward from that longitudinal axis immediately distal of barbs 436). This may further help to ensure that barbs 436 fully engage the wall of coronary artery 20.

Figures 21, 22:
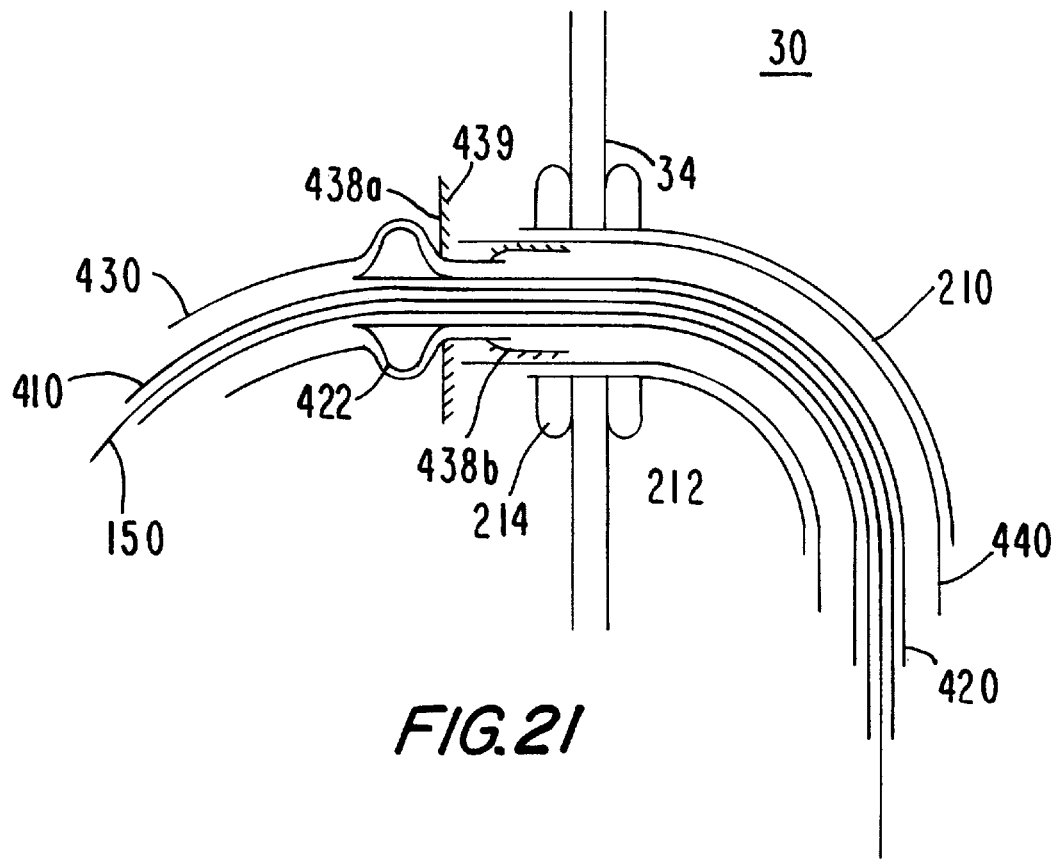
FIG. 21 is a view similar to another portion of FIG. 14 showing a still later stage in the FIG. 20 procedure.
FIG. 22 is a view similar to FIG. 21 showing an even later stage in the FIG. 21 procedure.

The next step is to deflate balloon 422. Then delivery tube 440 is withdrawn proximally until flap 438a (but not flap 438b) is distal of the distal end of the delivery tube. This allows flap 438a to spring radially out as shown in FIG. 21. Tube 420 is then withdrawn until balloon 422 is just distal of flap 438a. Then balloon 422 is inflated, producing the condition shown in FIG. 21.

The next steps are (1) to deflate distal balloon 214, (2) to proximally withdraw catheter 210 a short way, (3) tD proximally withdraw tube 420 to press flap 438a against the outer surface of the aorta wall, and (4) to proximally withdraw delivery tube 440 by the amount required to allow flap 438b to spring out against the interior of catheter 210, all as shown in FIG. 22. As a result of the above-described proximal withdrawal of tube 420, the barbs 439 on flap 438a are urged to enter the aorta wall tissue to help maintain engagement between flap 438a and the wall of the aorta. Inflated balloon 422 helps to set barbs 439 in the tissue when tube 420 is tugged proximally.

Figure 22A:
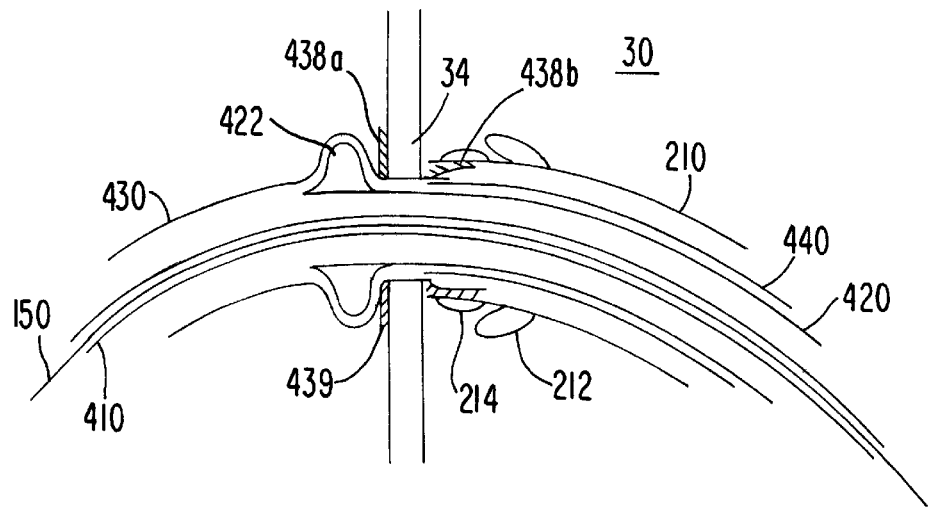
FIG. 22a is a view similar to FIG. 22 showing a still later stage in the FIG. 22 procedure.

The next step is to insert the distal portion of delivery tube 440 into the proximal end of conduit 430 as shown in FIG. 22a. The distal end of conduit 430 may be inserted all the way to the proximal end of balloon 422 (see FIG. 23 for a depiction of this). A purpose of this step is to subsequently help control the rate at which blood is allowed to begin to flow through conduit 430.

Figure 22B:
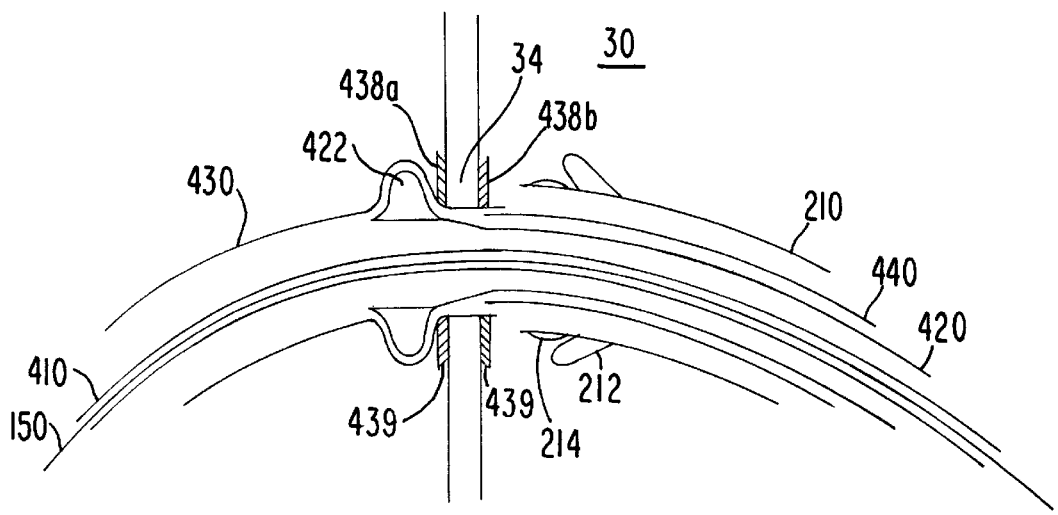
FIG. 22b is a view similar to FIG. 22a showing an even later stage in the FIG. 22a procedure.
Figure 23:
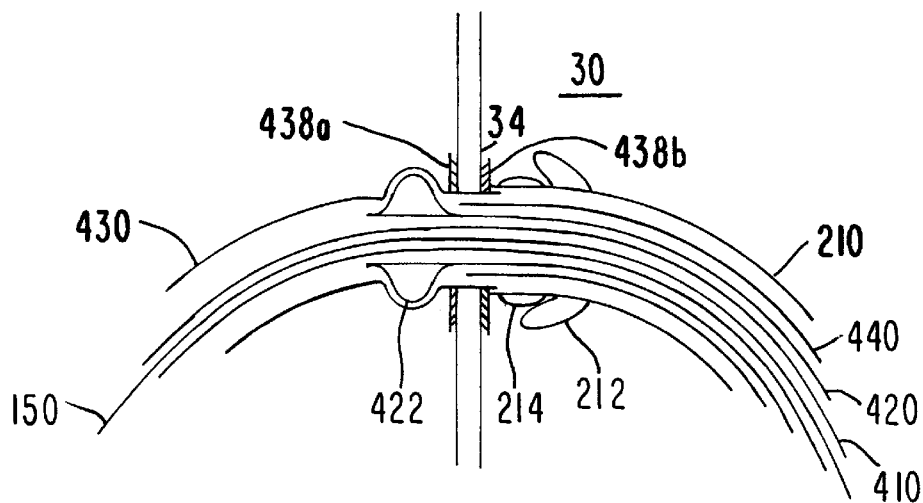
FIG. 23 is a view similar to FIG. 22b showing a still later stage in the FIG. 22b procedure.

The next step is to proximally withdraw catheter 210 by the amount required to release flap 438b to spring out against the interior of the wall of aorta 30 as shown in FIG. 22b. Catheter 210 may be subsequently pushed back against flap 438b as shown in FIG. 23 to help securely engage that flap against the aorta wall.

Figure 24:
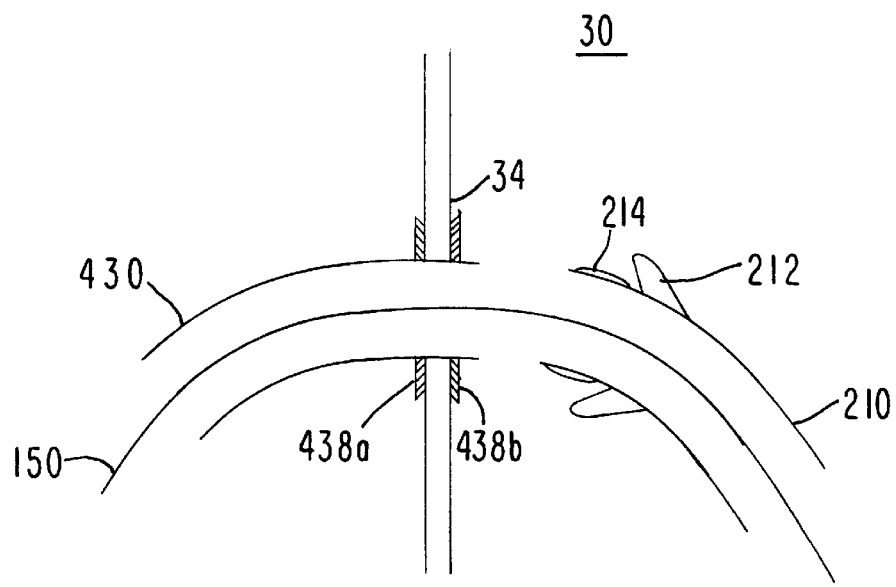
FIG. 24 is a view similar to FIG. 23 showing an even later stage in the FIG. 23 procedure.

Artificial graft conduit 430 is now fully established between aorta region 34 and coronary artery region 24. The next steps are therefore to deflate balloon 422 and proximally withdraw tube 420, to collapse tip 412 and proximally withdraw tube 410, and to proximally withdraw delivery tube 440. The proximal end of conduit 430 is now as shown in FIG. 24. As possible alternatives to what is shown in FIG. 24, the distal end of catheter 210 could be left pressed up against proximal flap 438b and/or the distal portion of delivery tube 440 could be left inside the proximal portion of conduit 430. If the latter possibility is employed, then delivery of the natural graft conduit (described below) can be through tube 440.

Figure 15A:
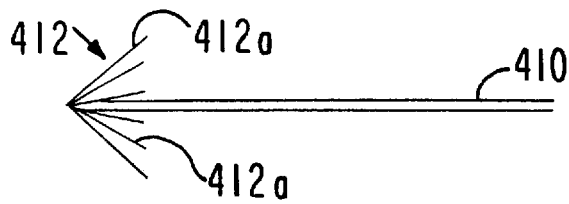
FIG. 15a is a simplified elevational view of a structure which can be used to provide part of the apparatus shown in FIG. 15.
Figure 15B:
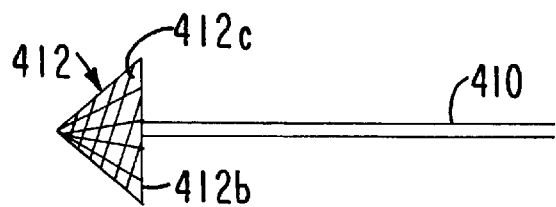
Figure 15C:
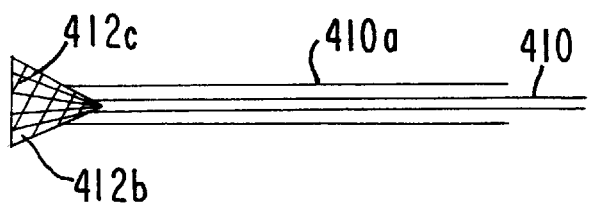
FIG. 15c is a view similar to FIG. 15b showing the FIG. 15b structure in another operational condition.

Several illustrative embodiments of collapsible tips 412 are shown in FIGS. 15a–15g. In the first embodiment (shown in FIGS. 15a–15c) a frame of wire struts 412a extends radially out and proximally back from the distal end of hypotube 410 (see especially FIG. 15a). This frame is covered with a somewhat elastic polymer cover 412b (FIG. 15b) which is provided with threads as indicated at 412c. For example, threads 412c may be made of one or more spirals of nitinol wire or other metal. When it is desired to collapse tip 412, another hypotube 410a (which is disposed around hypotube 410) is shifted distally relative to hypotube 410 to invert and collapse tip 412 as shown in FIG. 15c.

Figure 15D:
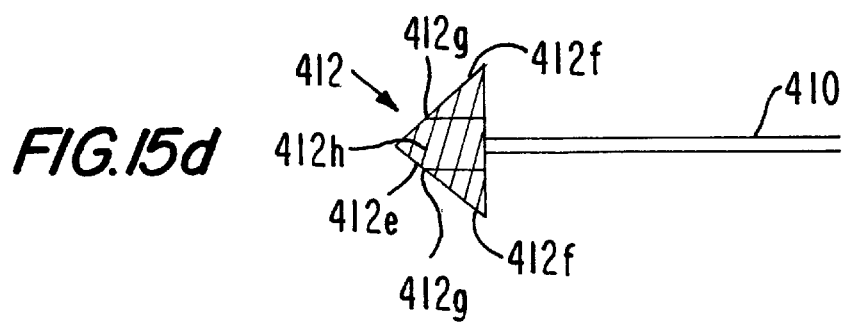
FIG. 15d is a simplified elevational view of an alternative structure which can be used to provide part of apparatus shown in FIG. 15.
Figure 15E:
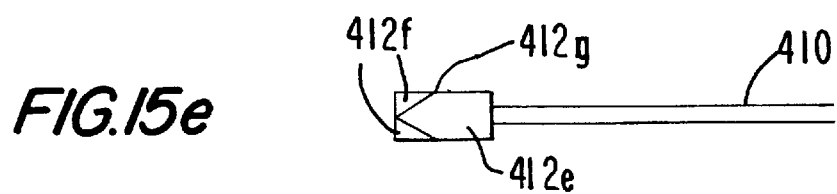
FIG. 15e is a view similar to FIG. 15d showing the FIG. 15d structure in another operational condition.

In the alternative embodiment shown in FIGS. 15d and 15e, tip 412 has a central main portion 412e attached to hypotube 410. Around the proximal portion of main portion 412e are a plurality of triangular shaped portions 412f, each of which is connected to main portion 412e by a hinge 412g. The outer surface of the tip is threaded as indicated at 412h. For example, in this embodiment tip 412 may be made of a plastic polymer material, and hinges 412g may be so-called "living" hinges between the various masses of the polymer. As soon as triangular portions 412f meet any resistance as tip 412 is withdrawn proximally, they pivot about their hinges 412g to the positions shown in FIG. 15e, thereby greatly reducing the circumferential size of the tip.

Figure 15F:
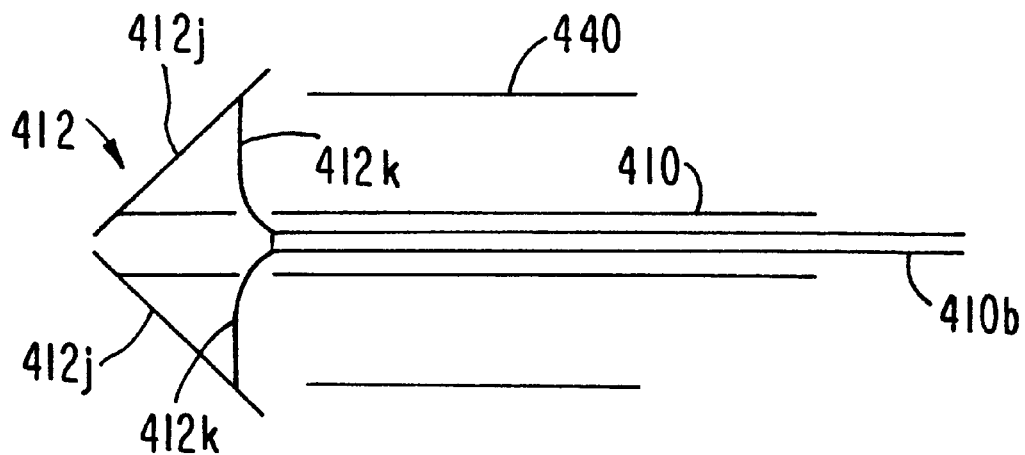
FIG. 15f is a simplified longitudinal sectional view of another alternative structure which can be used to provide part of the apparatus shown in FIG. 15.
Figure 15G:
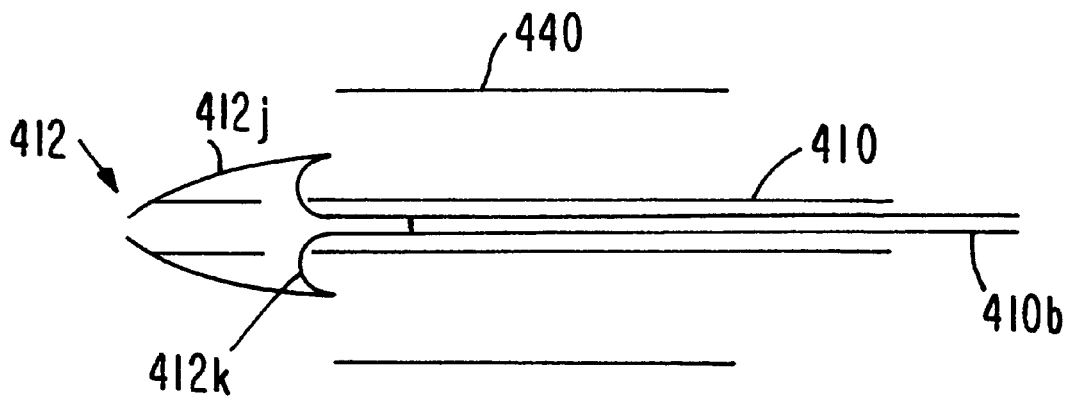
FIG. 15g is a view similar to FIG. 15f showing the FIG. 15f structure in another operational condition.

In the further alternative embodiment shown in FIGS. 15f and 15g, metal struts 412j are attached to the distal end of hypotube 410 so that they extend radially out and proximally back. Although not shown in FIGS. 15f and 15g, struts 412j are covered with a cover and thread, like the cover 412b and threads 412c shown in FIG. 15b and described above. A wire 412k connects a proximal portion of each strut 412j, through an aperture in hypotube 410, to the distal end of another hypotube 410b which is disposed inside hypotube 410. When wires 412k are relaxed as shown in FIG. 15f, struts 412j extend radially out beyond the circumference of delivery tube 440. When it is desired to collapse tip 412, hypotube 410b is pulled back proximally relative to hypotube 410 as shown in FIG. 15g. This causes wires 412k to pull struts 412j in so that the outer circumference of tip 412 is much smaller than the circumference of delivery tube 440.

Again, it should be mentioned that the use of a threaded, collapsible tip 412 as described above is only one of several possibilities. Other alternatives are discussed below after completion of the discussion of the illustrative procedure which is being described and which will now be further considered with reference to FIG. 25 and subsequent FIGS.

As has been mentioned, the illustrative procedure being described assumes that natural body conduit (e.g. a Length of the patient's saphenous vein that has been harvested for this purpose) is installed inside artificial conduit 430 after installation of the latter conduit. An illustrative assembly 500 for delivering a length of natural body conduit to installed conduit 430 is shown in FIG. 25.

Figure 25:
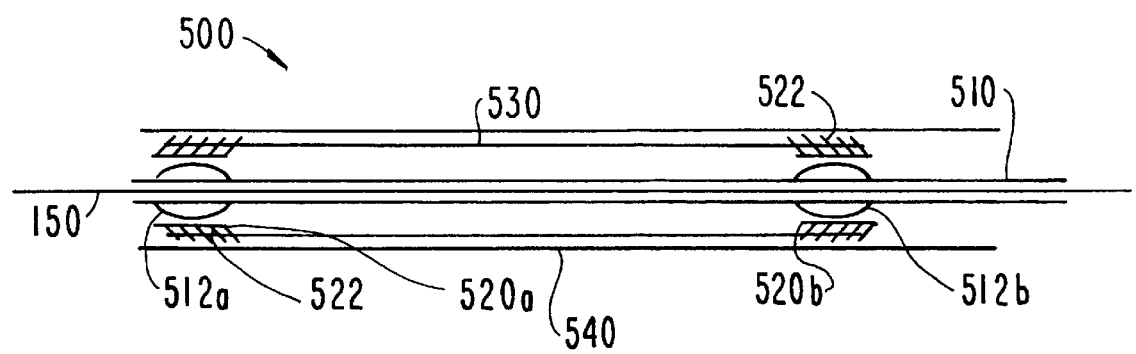
FIG. 25 is a simplified longitudinal sectional view of an illustrative embodiment of a portion of more apparatus in accordance with this invention.

As shown in FIG. 25, assembly 500 includes a tube 510 disposed around wire 150 so that tube 510 is freely movable in either direction along wire 150. Tube 510 has an inflatable annular balloon 512a near its distal end and another inflatable annular balloon 512b spaced in the proximal direction from balloon 512a. Tube 510 includes separate inflation lumens (not shown) for each of balloons 512 so that the balloons can be separately inflated and deflated. An annular collar structure or ring 520a is disposed concentrically around balloon 512a, and a similar annular collar structure or ring 520b is disposed concentrically around balloon 512b. Balloons 512 may be partly inflated. Each of rings 520 may have radially outwardly extending barbs 522. A length of natural body conduit 530 (e.g., saphenous vein as mentioned earlier) extends from ring 520a to ring 520b around the intervening portion of tube 510. Barbs 522 may extend through the portions of conduit 530 that axially overlap rings 520. A delivery tube 540 is disposed around conduit 530. In use, tubes 510 and 540 extend proximally (to the right as viewed in FIG. 25) out of the patient to permit the physician to remotely control the distal portion of assembly 500.

Although not shown in FIG. 25, assembly 500 may include a spring coil (similar to coil 450 in FIG. 36) extending between rings 520 inside of conduit 530 to help hold conduit 530 open and out against delivery tube 54) or subsequently out against conduit 430. Instead of balloons 512 being both in the same tube 510, balloon 512a may be on a relatively small first tube, while balloon 512b is on a larger second tube that concentrically surrounds the proximal portion of the first tube. The first and second tubes are axially movable relative to one another, thereby allowing the distance between balloons 512 to be adjusted for grafts 530 of different lengths.

Figure 26:
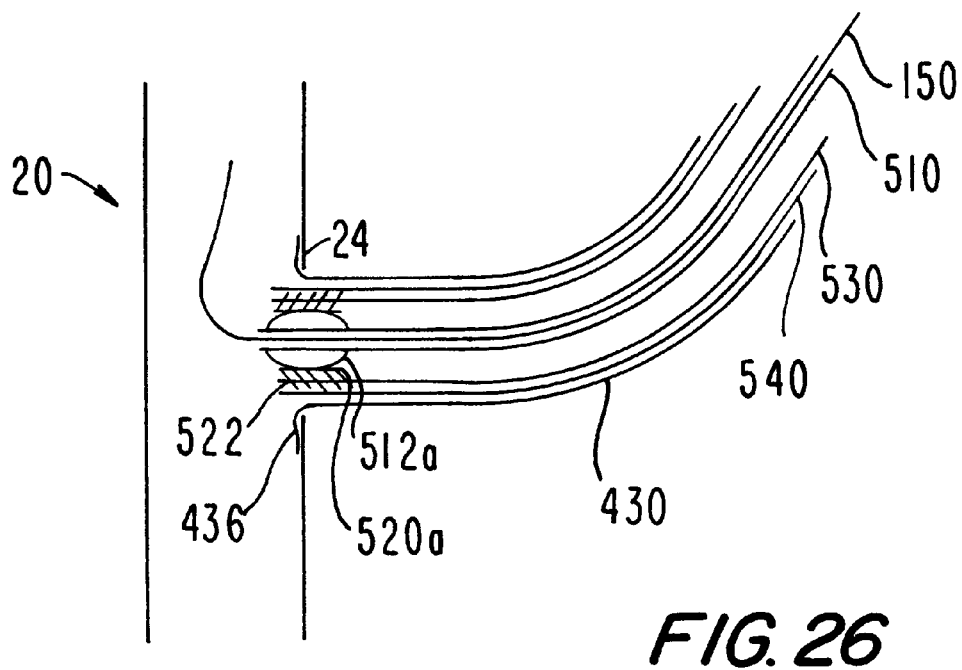
FIG. 26 is a view similar to FIG. 20 showing a later stage in the FIG. 24 procedure.
Figure 28:
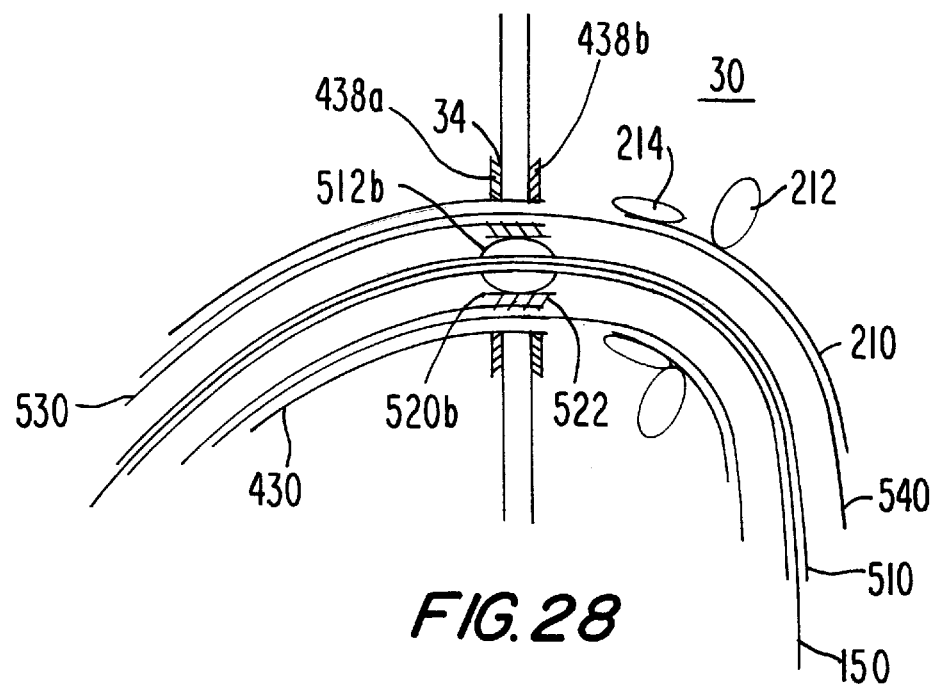
FIG. 28 is a view similar to FIG. 24 showing an even later stage in the FIG. 27 procedure.

Assembly 500 is employed by placing it on wire 150 leading into catheter 210. Assembly 500 is then advanced distally along wire 150 through catheter 210 and then into conduit 430 until the distal end of conduit 530 is adjacent the distal end of conduit 430 and the proximal end of conduit 530 is adjacent the proximal end of conduit 430. The condition of the apparatus at the distal end of assembly 500 is row as shown in FIG. 26. The condition of the apparatus at the proximal end of conduit 530 is as shown in FIG. 28.

Figure 27:
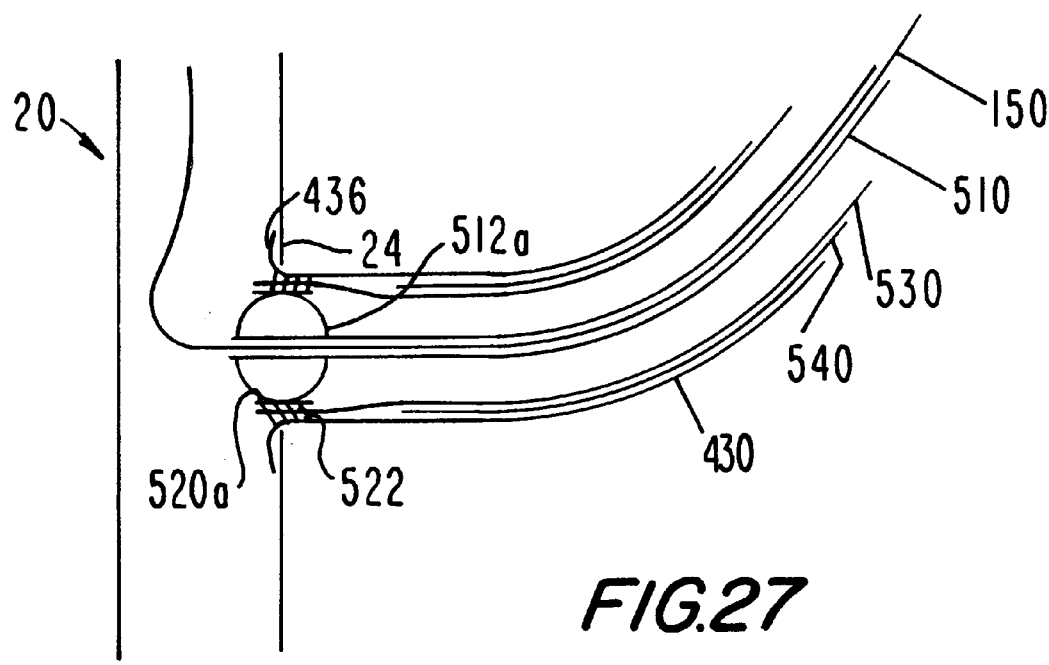
FIG. 27 is a view similar to FIG. 26 showing a still later stage in the FIG. 26 procedure.

The next step is to proximally withdraw delivery tube 540 so that the distal portion of conduit 530 and distal barbed ring 520a are no longer inside the distal portion of delivery tube 540. Then distal balloon 512a is inflated to circumferentially expand ring 520a and to set barbs 522 through conduit 530 into the surrounding portion of conduit 430 and coronary artery wall portion 24. This provides a completed anastomosis of the distal end of conduit 530 to coronary artery 20. FIG. 27 shows the condition of the apparatus at this stage in the procedure.

Figure 29:
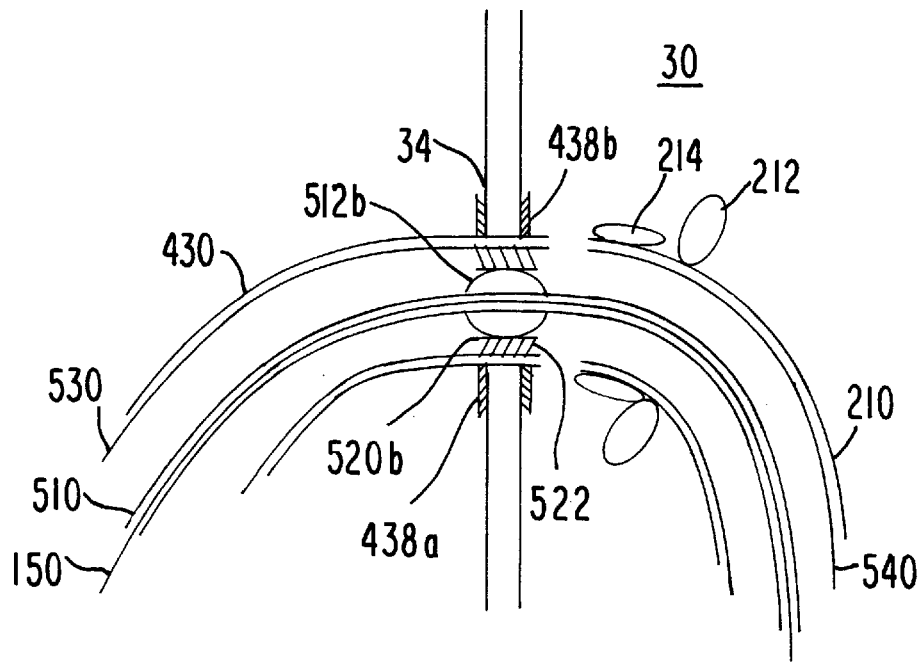
FIG. 29 is a view similar to FIG. 28 showing a still later stage in the FIG. 28 procedure.
Figure 30:
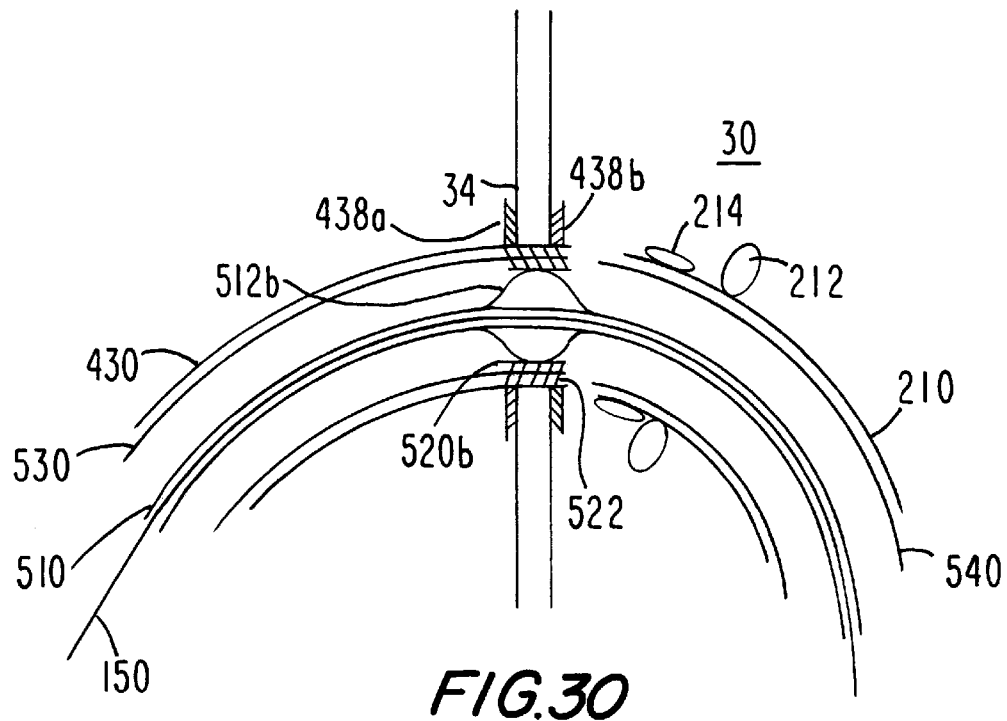
FIG. 30 is a view similar to FIG. 29 showing an even later stage in the FIG. 29 procedure.

The next step is to continue to proximally withdraw delivery tube 540 until the proximal end of conduit 530 and proximal ring 520b are no longer inside tube 540 (see FIG. 29). Then proximal balloon 512b is inflated to circumferentially expand ring 520b and thereby set barbs 522 through conduit 530 into the surrounding portion of conduit 430 and aorta wall portion 34 (see FIG. 30). This provides a completed anastomosis of the proximal end of conduit 530 to aorta 30.

Figure 31:
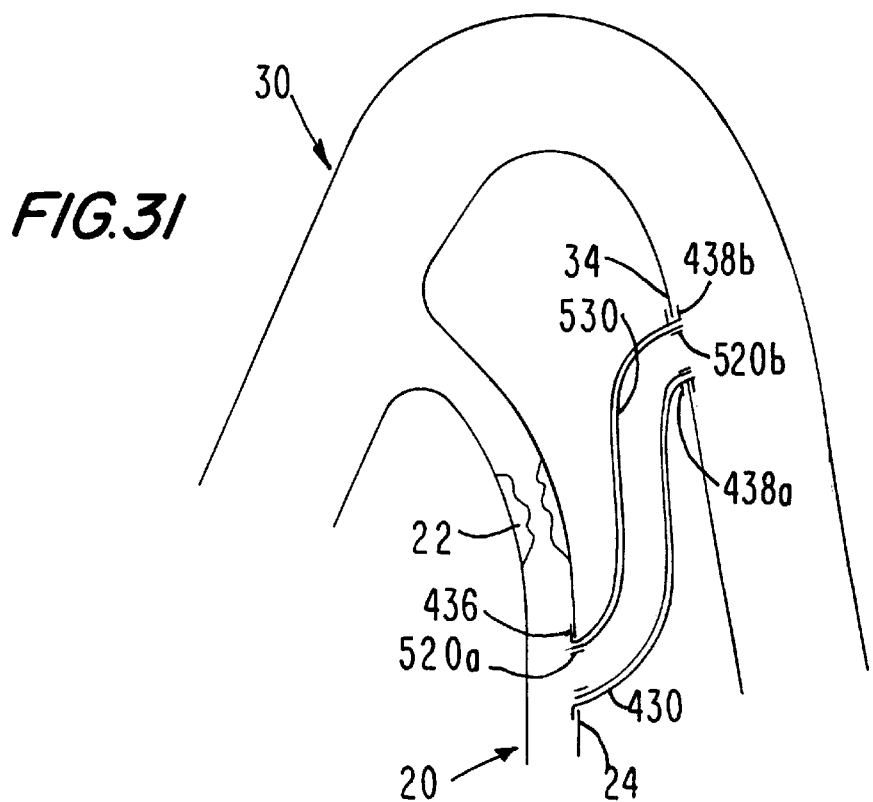
FIG. 31 is a view similar to FIG. 14 showing the end result of the procedure depicted in part by FIG. 30.

The next step is to deflate balloons 512a and 512b and proximally withdraw tube 510 and delivery tube 540 from the patient via catheter 210. Then wire 150 is withdrawn from the patient, either by pulling it proximally from catheter 210 or by pulling it proximally from elements 110 and 120. Lastly, elements 110, 120, and 210 are all proximally withdrawn from the patient to conclude the procedure. The bypass that is left in the patient is as shown in FIG. 31. This bypass extends from aorta 30 at location 34 to coronary artery 20 at location 24. The bypass includes natural body conduit 530 inside artificial graft conduit 430. One end of the bypass is anchored and anastomosed to coronary artery 20 by barbs 436 and ring 520a. The Dther end of the bypass is anchored and anastomosed to aDrta 30 by flaps 438 and ring 520b.

Figure 32:
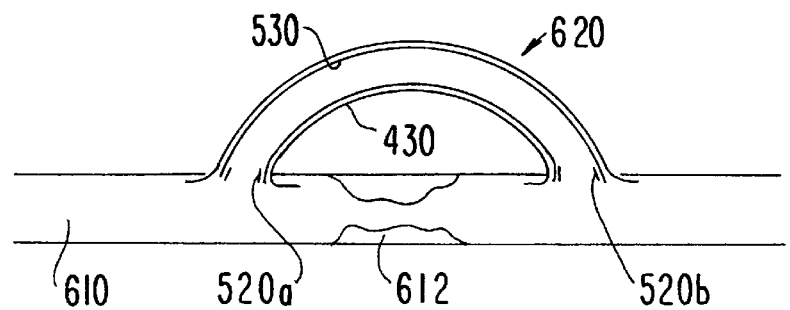
FIG. 32 is a simplified longitudinal sectional view showing an end result similar to FIG. 31 but in a different context.

The particular uses of the invention that have been described in detail above are only illustrative of many possible uses of the invention. Other examples include same-vessel bypasses in the coronary area and vessel-to-vessel and same-vessel bypasses in other portions of the circulatory system (including neurological areas, renal areas, urological areas, gynecological areas, and peripheral areas generally). A same-vessel bypass is a bypass that extends from one portion of a vessel to another axially spaced portion of the same vessel. In FIG. 32, bypass 620 is a same-vessel bypass around a narrowing 612 in vessel 610. For ease of comparison to previously described embodiments, the various components of bypass 620 are identified using the same reference numbers that are used for similar elements in FIG. 31. The invention is also applicable to procedures similar to any of those mentioned above, but for non-circulatory systems such as urological tubing.

Figure 33:
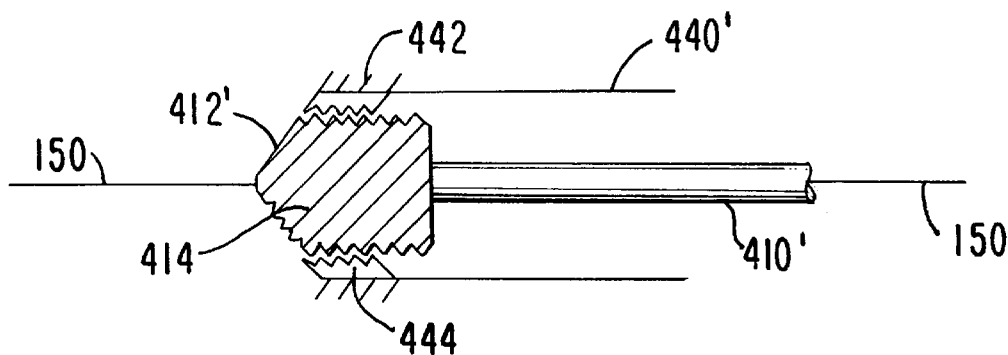
FIG. 33 is a simplified longitudinal sectional view showing a possible alternative construction of portions of the apparatus showing in FIG. 15.

It has been mentioned that the collapsible tip structures shown, for example, in FIGS. 15–15g are illustrative of only one of several possible approaches to providing a structure that can penetrate the wall of coronary artery 20 from outside the artery. Another example of a suitable structure is shown in FIG. 33. To facilitate comparison to FIG. 15, FIG. 33 uses reference numbers with primes for elements that are generally similar to elements identified by the corresponding unprimed reference numbers in FIG. 15.

In the embodiment shown in FIG. 33 distal tip 412' has external threads 414 for helping to grip and dilate tissue such as the wall of coronary artery 20 as tip 412' is rotated about wire 150 by rotation of proximally extending tubular shaft 410'. Threads 414 continue as threads 442 on the exterior of the distal portion of tube 440'. Threads 414 also threadedly engage with threads 444 on the interior of the distal portion of tube 440'. Thus when both of structures 410' and 440' are rotated together, threads 414 and 442 tend to pull tip 412' and then the distal portion of tube 440' into and through the wall of coronary artery 20. In the course of this, threads 412' transfer the tissue to threads 442. Thereafter, structure 410' can be removed from structure 440' by rotating structure 410' in the direction relative to structure 440' that causes threads 414 and 444 to cooperate to shift tip 412' proximally relative to structure 440'. When tip 412' has thus shifted proximally beyond threads 444, elements 410' and 412' can be pulled proximally out of the patient. Tube 440', which remains in place through the coronary artery wall, can thereafter be used as a guide tube for delivery of a graft structure (such as 430 (FIGS. 15–17)) and associated instrumentation (such as structure 420 (e.g., FIGS. 15 and 17)) to the operative site.

Figure 34:
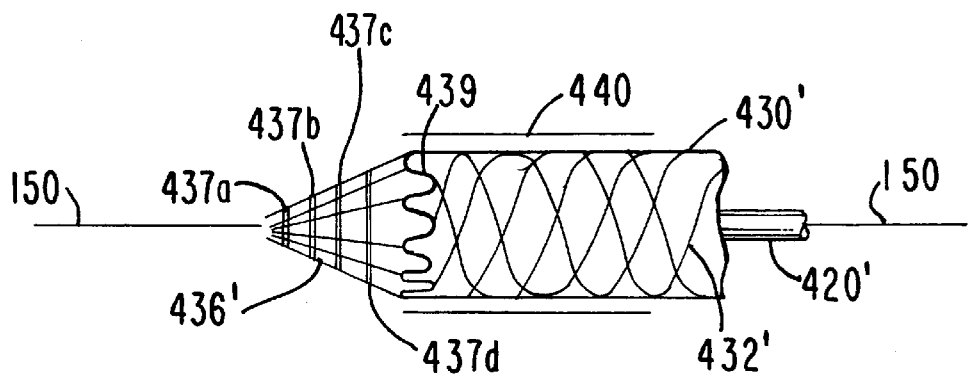
FIG. 34 is a simplified elevational view (partly in section) showing another possible alternative construction of portions of the FIG. 15 apparatus.
Figure 35:
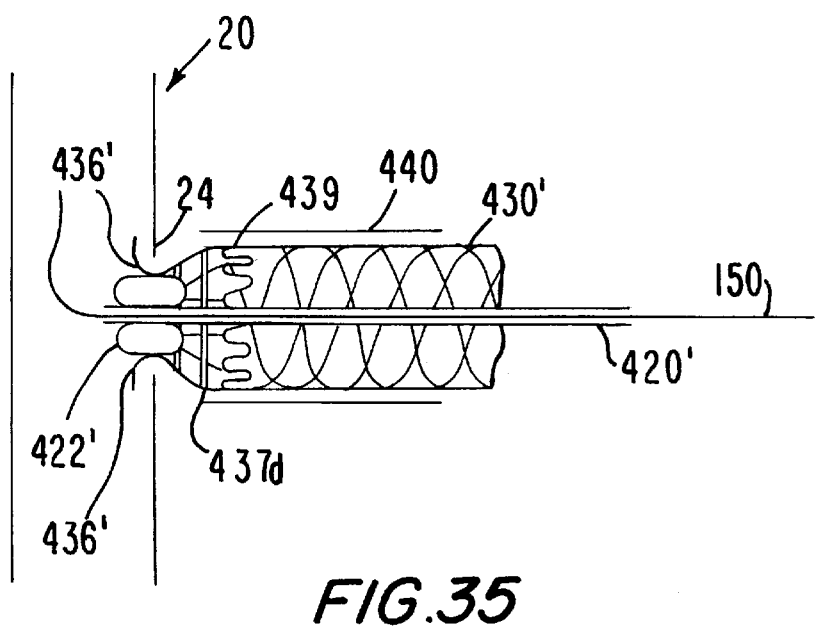
FIG. 35 is a simplified longitudinal sectional view of the FIG. 34 apparatus in another operating condition.

Another illustrative alternative embodiment of some of the instrumentation shown in FIG. 15 is shown in FIGS. 34 and 35. Once again, to facilitate comparison to FIG. 15, FIGS. 34 and 35 use reference numbers with primes for elements that are generally similar to elements identified by the corresponding unprimed reference numbers in FIG. 15. In the embodiment shown in FIGS. 34 and 35 barbs 436' are connected to the distal end of a serpentine ring 439 which is connected in turn to the distal end of frame 432'. Barbs 436' are initially held in the form of a distally pointed cone by yieldable bands 437a, 437b, 437c, and 437d. As elsewhere along graft conduit 430', the spaces between barbs 436' are substantially filled by a highly elastic material such as silicone rubber. Bands 437 may be made of a polymeric or other suitable yieldable material. Alternatively, bands 437 could be serpentine metal members that yield by becoming straighter. Bards 437 are initially strong enough to prevent barbs 436' from flaring radially outward from conduit 430' as the barbs are resiliently biased to do. However, bands 437 can be made to yield by inflating balloon 422' (on the distal end of tube 420') inside the annulus of barbs 436'.

Barbs 436' can be forced through tissue such as the wall of coronary artery 20 in their initial cone shape. Sufficient pushing force can be applied to the cone of barbs 436' in any of several ways. For example, tube 420' may be metal (e.g., stainless steel) hypotube which can transmit pushing force to the cone of barbs 436' by inflating balloon 422' to trap the base of the cone between balloon 422' and tube 440. Additional pushinag force may then also be applied via tube 440 itself.

When a sufficient portion of the height of the cone of barbs 436' is through the coronary artery wall, balloon 422' is inflated inside the cone as shown in FIG. 35 to cause bands 437 to yield. This allows barbs 436' to flare radially outward inside the coronary artery, thereby anchoring the distal end of conduit 430' to the artery. Bands 437 may be made progressively weaker in the distal direction to facilitate prompt yielding of distal bands such as 437a and 437b in response to relatively little inflation of balloon 422', whereas more proximal bands such as 437c and 437d do not yield until somewhat later in response to greater inflation of balloon 422'. This progression of yielding may help ensure that the annulus of barbs flares out in the desired trumpet-bell shape inside the coronary artery.

Figure 36:
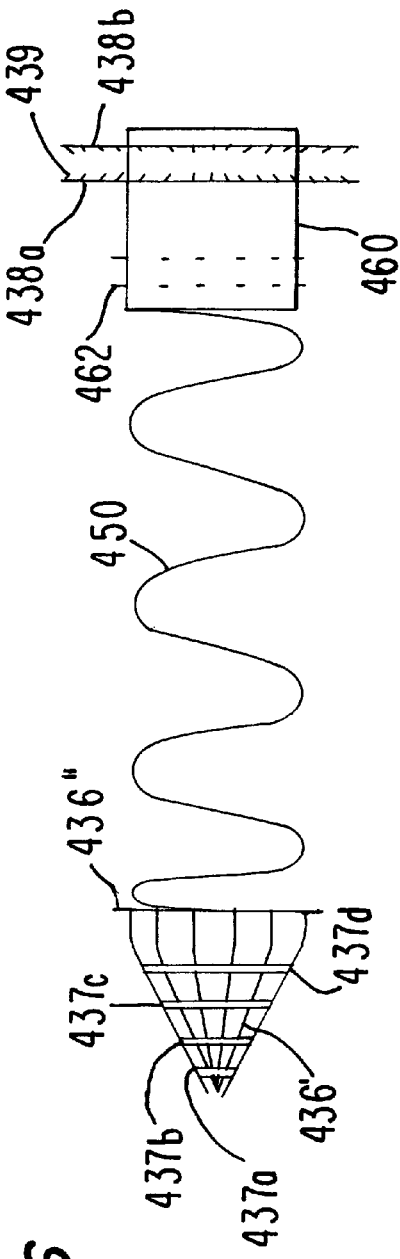
FIG. 36 is a simplified elevational view of apparatus which can be used as an alternative to certain apparatus components shown in FIGS. 15 and 17.
Figure 37:
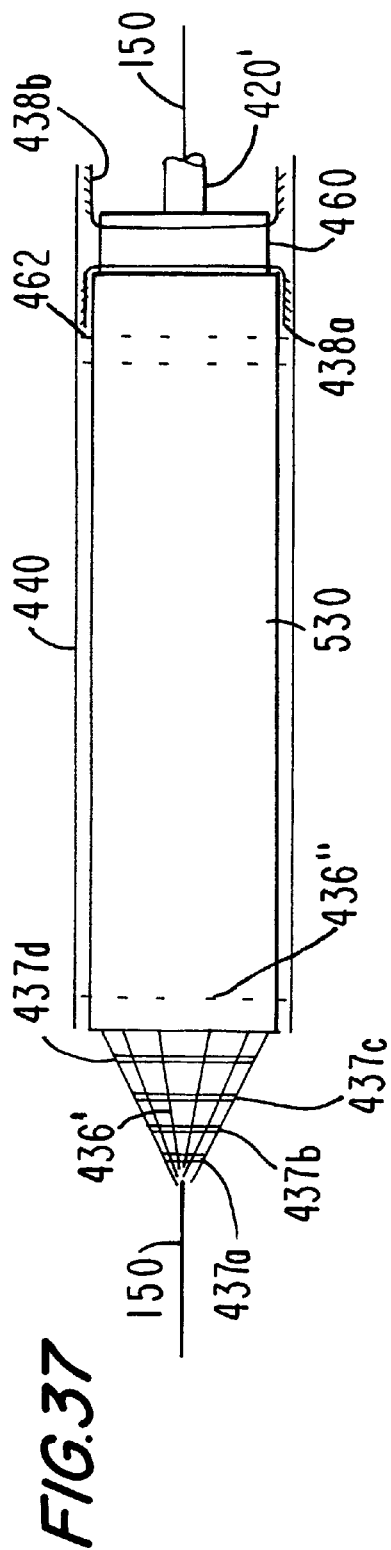
FIG. 37 is a simplified elevational view (partly in section) showing additional components with the FIG. 36 apparatus.

FIGS. 36 and 37 illustrate another possible use of a cone structure like that shown in FIGS. 34 and 35, as well as illustrating other possible aspects of the invention. These FIGS. illustrate a structure that can be used to deliver an artificial graft conduit, or a natural graft conduit, or both an artificial graft conduit and a natural graft conduit simultaneously (e.g., with the natural conduit coaxially inside the artificial conduit). In the particular case shown in FIGS. 36 and 37 it is assumed that only natural graft conduit is being delivered, but it will be readily apparent that artificial graft conduit could be substituted for or added outside the natural graft conduit.

In the embodiment shown in FIGS. 36 and 37 the cone of barbs 436' is mounted on the distal end of a highly elastic coil spring 450. The proximal end of coil 450 is attached to ring 460. The cone of barbs 436' is provided with additional, relatively short, radially outwardly projecting barbs 436" near the proximal base of the cone. As shown in FIG. 37, barbs 436" extend into and/or through the distal portion of a length of graft tubing 530, which (as has been mentioned) is assumed in this case to be natural body organ tubing such as saphenous vein. Ring 460 is similarly provided with radially outwardly extending barbs 462 which extend into and/or through the proximal portion of graft conduit 530. Ring 460 also includes resilient radially outwardly extending annular flaps 438a and 438b with barbs 439, all similar to correspondingly numbered elements in FIG. 16. Spring 450, which is inside conduit 530 between the cone of barbs 436' and ring 460, helps to support and hold open the graft conduit. Structure 420' (similar to structure 420' in FIGS. 34 and 35 and including balloon 422' as shown in those FIGS.) is disposed around wire 150 inside structures 436', 450, 460, and 530. Delivery tube 440 is disposed around conduit 530.

The embodiment shown in FIGS. 36 and 37 illustrates a structure which can be used to deliver and install natural body organ conduit without any full length artificial graft conduit being used. In a manner similar to what is shown in FIGS. 34 and 35, the structure shown in FIG. 37 is delivered to the operative site via wire 150. The cone of barbs 436' is forced through the wall of coronary artery 20 and then flared radially outward inside the coronary artery to anchor the distal end of the graft conduit to that artery. The distal end of delivery tube 440 is pulled back as needed to aid in attachment of the distal end of the graft structure. Attachment of the proximal end of the graft structure to the wall of aorta 30 is performed similarly to what is shown in FIGS. 21–24. Accordingly, with distal flap 438a just outside the wall of aorta 30, delivery tube 440 is pulled back proximally to expose that flap. Flap 438a is thereby released to spring out and engage the outer surface of the aorta wall. After that has occurred, proximal flap 438b is adjacent the inner surface of the aorta wall. Tube 440 is pulled back proximally even farther to expose flap 438b so that it can spring out and engage the inner surface of the aorta wall. Natural body organ graft 530 is now fully installed in the patient. Structures 436', 450, and 460 remain in place in the patient to help anchor the ends of graft conduit 530 and to help hold open the medial portion of that conduit.

In embodiments like FIGS. 36 and 37, coil 450 is optional. If coil 450 is used, its ends may or may not be attached to structures 436 and/or 460.

A coil like coil 450 can be used in other embodiments of the invention. For example, a coil like 450 could be used between rings 520a and 520b in embodiments like that shown in FIG. 25 to help hold open graft conduit 530 in that embodiment.

Figure 38:
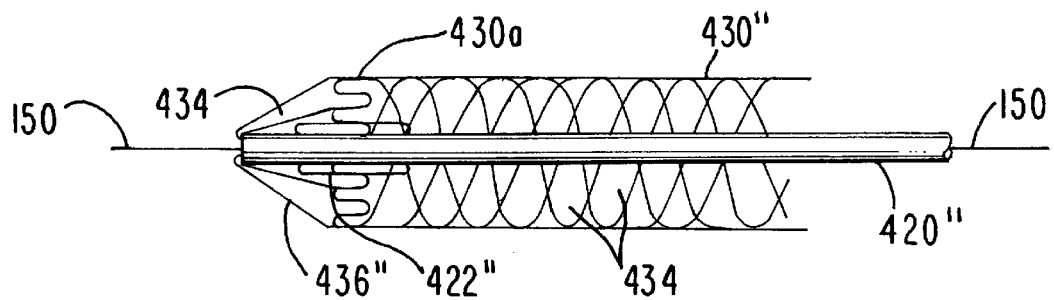
FIG. 38 is a simplified longitudinal sectional view showing still another possible alternative construction of portions of the FIG. 15 apparatus.

Still another illustrative alternative embodiment of some of the instrumentation shown in FIG. 15 is shown in FIG. 38. To facilitate comparison to FIG. 15, FIG. 38 uses reference numbers with double primes for elements that are generally similar to elements identified by the corresponding unprimed reference numbers in FIG. 15. In the embodiment shown in FIG. 38, the distal end of artificial graft conduit 430" is attached to expandable ring 430a. Elongated barbs 436" extend distally from the distal end of ring 430a. The distal ends of barbs 436" are turned back in the proximal direction and extend just far enough into the distal end of tube 420" to be releasably retained by that tube. Barbs 436" are resiliently biased to extend radially outward from ring 430a, but are initially restrained from doing so by the presence of their distal end portions in the distal end of tube 420". Thus barbs 436" initially form a distally pointing cone that can be pushed through tissue such as the wall of coronary artery 20 in the same manner that has been described above in connection with FIGS. 34–37. Structure 420", which may be metal (e.g., stainless steel) hypotube with an inflatable annular balloon 422" near its distal end, may be used to help push the cone through the tissue.

After the distal portion of the cone of barbs 436" has been pushed through the wall of coronary artery 20, tube 420" is shifted proximally relative to the barbs to release the distal end portions of the barbs. This allows barbs 436" to spring radially outward from ring 430a inside coronary artery 20, thereby anchoriing the distal end of the graft conduit in the coronary artery. Ring 430a can then be circumferentially expanded to increase the size of the connection between coronary artery 20 and the distal portion of the graft conduit.

Figure 39:
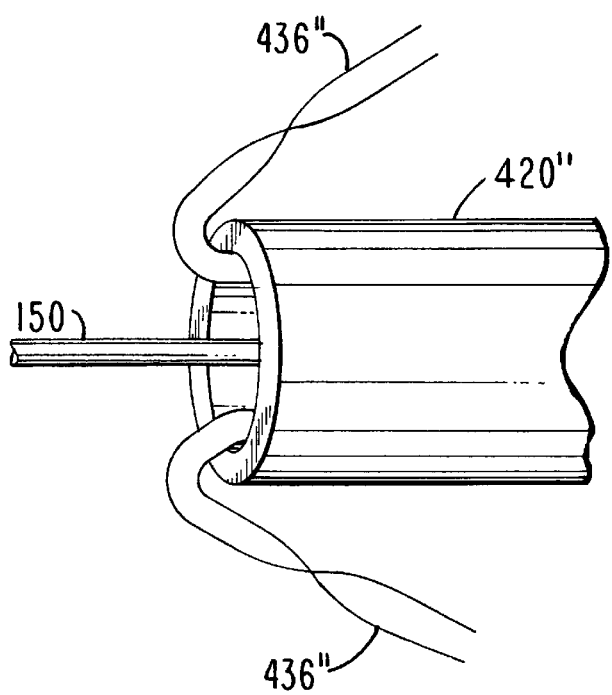
FIG. 39 is a simplified elevational view showing in more cetail a possible construction of a portion of the FIG. 38 apparatus.

If desired, each of barbs 436" may he twisted 180° as shown in FIG. 39 before it enters the distal end of tube 420". This promotes turning of the extreme distal end portions of the barbs toward the coronary artery wall when the barbs are released from tube 420".

Ring 430a and barbs 436" may be made of any suitable material such as any 300-series stainless steel (e.g., 316L stainless steel). Another material that may be suitable for barbs 436" is nitinol. As in previously described embodiments, the elastic cover 434 that forms part of conduit 430" preferably extends to regions 430a and 436".

A preferred artificial graft (such as conduit 430 in FIG. 16) in accordance with this invention includes an open frame structure (such as 432 in FIG. 16). This frame structure may have any desired shape such as a tube, a flat or contoured sheet, etc. The frame structure may be formed in any suitable way such as by cutting apertures in an initially imperforate structure; forming a mesh of strands of frame material; braiding, knitting, weaving, or felting together strands of frame material; etc. The frame material is preferably an elastic material. Preferred materials are metal, although polymeric materials may also be used. The presently most preferred material is nitinol, and the presently most preferred structure for the frame of a tubular graft is a braid of nitinol wires.

The above-described graft frame is preferably covered with a covering of elastic rubber-like material which substantially fills the apertures in the frame as at 434 in FIG. 16. The covering may be inside the frame structure, outside the frame structure, or both inside and outside the frame structure. Preferred rubber-like materials for the covering are polymeric materials, especially polymeric rubber materials. The presently most preferred rubber-like material is silicone. Examples of other suitable rubber-like materials are stretchable urethane, stretchable PTFE, natural rubber, and the like. For some applications it may be desirable to make the covering porous. Other applications may not benefit from such porosity. Thus the covering can be made either porous or non-porous as desired.

The graft structure may include one or more coatings over the above-described covering. In the case of a tubular graft the coating(s) may be inside the tube, outside the tube, or both inside and outside the tube. Possible coating materials include bio-compatible materials and/or drugs. Examples include hydrophylic polymers such as hydrophylic polyurethane (to create a lubricious surface), parylene (a polymer commonly used to coat pacemakers), PTFE (which may be deposited from a PTFE vapor using a process that is sometimes called vapor transport), the drug Heparin (a common anti-coagulant), collagen, human cell seeding, etc. One purpose of such a coating may be to give the coated surface a very high degree of bio-compatibility and/or a very hicgh degree of smoothness.

The graft structure may or not include hooks, barbs, flaps, or other similar structures for such purposes as helping to anchor the graft in the body, provide anastomoses between the graft and existing body tubing, etc. Several examples of such structures are shown and described elsewhere in this specification. If provided, such hooks, barbs, flaps, and the like may be extensions of the frame structure or may be molded with or otherwise added to the frame or covering.

The most preferred grafts of this invention (e.g., those with a nitinol frame and silicone covering) are highly elastic. The elastic nature of these graft structures allows them to be deployed less invasively (e.g., intravascularly or at least percutaneously). This avoids or reduces the need for surgical implantation. For example, a tubular graft of this construction can be stretched to several times its relaxed length, which greatly reduces its diameter. This facilitates intravascular delivery of the graft. When released from the delivery apparatus, the graft automatically returns to its relaxed length and diameter, with no ill-effects of any kind from its previous deformation. If installed in the circulatory system, the graft is so flexible and elastic that it pulsates in response to pressure waves or pulses in the blood flow. This distensibility of the graft may help prevent blood clots. Coatings that are used on the graft are preferably similarly distensible.

In the grafts of this invention that are made with a braided nitinol wire frame and a silicone covering, the preferred wire diameter is in the range from about 0.0005 to about 0.01 inches. An especially preferred wire diameter is about 0.002 inches. The preferred silicore covering thickness is in the range from about 0.00025 to about 0.1 inches. Two covering layers may be used: one inside and one outside the frame structure. If the covering is made porous, the preferred pore size is in the range from about 1 to about 500 microns. An especially preferred pore size is about 30 microns. The preferred covering porosity is in the range from about 50% to about 95%. In other words, from about 50% to about 95% of the volume of the covering is pore space. If any coatings are applied to the graft, they are preferably thinner than the covering.

For the preferred grafts of this invention, a preferred manufacturing process in accordance with the invention includes placing or forming the frame structure of the graft on a form (e.g., a rod-like mandrel or tube in the case of the frame for a tubular graft). The form (e.g., mandrel) may be coated with a release agent such as polyvinyl alcohol. The covering is then applied to the frame or the form. The covering is cured, and the frame and covering are removed from the form. Any release agent that remains on the graft is removed. For example, if the release agent is polyvinyl alcohol, it may be removed by boiling the graft in water. If a covering is desired on the inside of the graft, a layer of the covering material may be applied to the form before the frame structure is placed or formed on the form. The form may be provided with a very smooth surface to give the finished graft a correspondingly smooth surface. For example, a very smooth mandrel may be used to give the inside of a tubular graft a very smooth surface.

If one or more coatings are desired on the graft, the coating may be done at any suitable time. For example, the coating may be done after the graft has been removed from the form. The coating or coatings may be applied using any suitable technique such as dipping, electrostatic spraying, vapor transport, in vitro cell reproduction, etc.

A preferred method in accordance with the invention for making the graft covering porous is to mix particles of another material with the covering material before applying the covering material to the frame. The particulate material is selected as one which is stable or at least relatively stable during curing of the covering on the frame, but which can then be removed from the cured covering to leave the covering with the desired porosity. For example, the particulate material may be a salt such as ammonium carbonate, which is relatively stable at temperatures substantially below about 78° C., but which vaporizes relatively rapidly at an elevated temperature (i.e., about 78° C.) that is not harmful to the cured coating material. Any other particulate material that can be removed by vaporization or solution can be used. For example, the particulate material may be removed by dissolving in water or another solvent, by exposure to air or another vaporization medium, by heat, by vacuum, or by any other suitable means.

Porosity of the covering is believed to be beneficial for circulatory system grafts. It may promote growth of a cell structure on the inside wall of the graft. And in all uses, porosity may promote better adherence of the above-mentioned coatings to the graft.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired. The manner in which radiologic elements and techniques are used for observation of the apparatus inside the patient may vary. For example, radiologic fluids may be injected into the patient through various lumens in the apparatus to help monitor the location of various apparatus components in the patient, and/or radiologic markers (of which the above-described markers such as 112, 124, and 154 are examples) may be provided anywhere on the apparatus that may be helpful to the physician.

The invention claimed is:

1. The method for forming a tubular graft connection between first and second sections of a patient's existing tubular body organ structure comprising the steps of:
    passing a length of graft tubing axially along an interior lumen of a portion of said existing structure to place a first end portion of said length of qraft tubing inside said first section of said existing structure;
    causing said first end portion of said length of graft tubing to emerge from inside to outside of said first section of said existing structure via an aperture in a wall of said first section;
    extending said first end portion of said length of graft tubing outside of said existing structure to an aperture in a wall of said second section of said existing structure;
    securing said first end portion of said length of graft tubing to said second section of said existing structure; and
    securing a portion of said length of graft tubing which is axially spaced from said first end portion to said first section of said existing structure.

2. The method defined in claim 1 wherein each of said steps is at least partly controlled from outside of the patient via instrumentation that passes through said existing structure to reach at least one of said first and second sections.

3. The method defined in claim 1 wherein said step of securing said first end portion of said length of graft tubing comprises the step of:
    forming an anastomosis between said first end portion of said length of graft tubing and said second section of said existing structure.

4. The method defined in claim 1 wherein said step of securing a portion of said length of graft tubing which is axially spaced from said first end portion comprises the step of:
    forming an anastomosis between said portion which is axially spaced and said first section of said existing structure.

5. The method defined in claim 1 wherein said length of graft tubing includes artificial graft tubing.

6. The method defined in claim 1 further comprising the step of:
    removing a length of the patient's natural body organ tubing for use as at least part of the length of graft tubing.

7. The method defined in claim 6 further comprising the step of:
    disposing the natural body organ tubing substantially coaxially inside artificial graft tubing to provide said length of graft tubing.

8. The method defined in claim 1 wherein said steps of passing, causing, and extending are preceded by the step of:
    positioning a longitudinal structure along the interior lumen of said portion of said existing structure and out of said existing structure via said aperture in said first section to said aperture in said second section.

9. The method defined in claim 8 wherein said steps of passing, causing, and extending are at least partly performed by moving said length of graft tubing along said longitudinal structure.

10. The method defined in claim 9 wherein said length of graft tubing is placed coaxially around said longitudinal structure in order to move said length of graft tubing along said longitudinal structure.

11. The method defined in claim 8 wherein said positioning step comprises the steps of:
    passing a first length of the longitudinal structure along the interior lumen of said portion of said existing structure so that a distal portion of said first length extends out from said existing structure via said aperture in said first section;
    passing a second length of longitudinal structure along the interior lumen of a part of said existing structure which is at least partly different from said portion of said existing structure so that a distal portion of said second length extends out from said existing structure via said aperture in said second section; and
    interengaging said distal portion of said first length and said dislal portion of said second length at an interengagement location which is between said aperture in said first section and said aperture in said second section and outside of said existing structure.

12. The method in claim 11 wherein said positioning step further comprises the step of:
    after performing said interengaging step, axially shifting the interengaging first and second lengths so that the interengagement location is no longer between said aperture in said first section and said aperture in said second section outside of said existing structure.

13. The method defined in claim 12 wherein said axially shifting is performed until said interengagement location is outside of the patient.

14. The method defined in claim 1 wherein said steps of passing and causing are preceded by the step of:
    positioning a tubular instrument along the interior lumen of said portion of said existing structure and out of said existing structure via said aperture in said first section.

15. The method defined in claim 14 wherein said steps of passing, causing, and extending are at least partly performed by moving said length of draft tubing through said tubular instrument.

16. The method defined in claim 1 wherein said length of graft tubing is disposed in a delivery tube instrument during said passing, causing, and extending steps, and wherein said method further comprises the step of removing said delivery tube instrument from said length of graft tubing prior to completion of said securing steps.

17. The method defined in claim 1 wherein said length of graft tubing includes selectively operable fasteners, and wherein said step of securing said first end portion comprises the step of:

operating fasteners adjacent to said second section to fasten said first end portion to said second section.

18. The method defined in claim 17 wherein said operating step causes said fasteners adjacent to said second section to extend radially outward from said length of graft tubing into said second section.

19. The method defined in claim 17 wherein said fasteners adjacent to said second section are disposed in an annular array which is substantially concentric with said length of graft tubing, and wherein said operating step comprises the step of:

circumferentially expanding said annular array into engagement with said second section.

20. The method defined in claim 17 wherein said operating step comprises the steps of:

disposing an inflatable member inside said length of graft tubing adjacent to said fasteners adjacent to said second section; and inflating said inflatable member to help said fasteners securely engage said second section.

21. The method defined in claim 20 wherein said operating step further comprises the step of:

deflating said inflatable member after performing said inflating step.

22. The method defined in claim 1 wherein said length of graft tubing includes selectively operable fasteners, and wherein said step of securing a portion of said length of graft tubing to said first section comprises the step of:

operating fasteners adjacent to said first section to fasten said portion of said length of graft tubing which is axially spaced from said first end portion to said first section.

23. The method defined in claim 22 wherein said operating step causes said fasteners adjacent to said first section to extend radially outward from said length of graft tubing into said first section.

24. The method defined in claim 22 wherein said fasteners adjacent to said first section are disposed in an annular array which is substantially concentric with said length of graft tubing, and wherein said operating step comprises the step of:

circumferentially expanding said annular array into engagement with said first section.

25. The method defined in claim 22 wherein said operating step comprises the steps of:

disposing an inflatable member inside of said length of graft tubing adjacent to said fasteners adjacent to said first section; and inflating said inflatable member to help said fasteners securely engage said first section.

26. The method defined in claim 25 wherein said operating step further comprises the step of:

deflating said inflatable member after performing said inflating step.

27. A method of providing a tubular graft connection between first and second tubular bode organ sections in a patient comprising the steps of:

inserting a first elongated instrument substantially coaxially into said first tubular body organ section;

inserting a second elongated instrument substantially coaxially into said second tubular body organ section;

extending a first longitudinal structure from said first instrument so that a distal portion of said first structure passes through a wall of said first tubular body organ section;

extending a second longitudinal structure from said second instrument so that a distal portion of said second structure passes through a wall of said second tubular body organ section;

interengaging said distal portions of said first and second structures outside of said first and second tubular body organ sections; and extending a length of graft tubing along at least one of said first and second structures so that said length of graft tubing extends between said first and second body organ sections outside of said first and second body organ sections.

28. The method defined in claim 27 wherein said interengaging step takes place inside the body of the patient, and wherein said length of graft tubing extends between said first and second body organ sections outside of said first and second body organ sections but inside the body of the patient as a result of performing said step of extending a length of graft tubing.

29. The method defined in claim 27 wherein all of said extending and interengaging steps are performed inside the body of the patient under remote control from outside the patient via at least one of said first and second instruments.

30. The method defined in claim 27 further comprising the step of:

after performing said interengaging step, longitudinally displacing the interengaged first and second structures so that said one of said first and second structures extends continuously between said first and second tubular body organ sections outside of said first and second tubular body organ sections.

31. The method defined in claim 27 further comprising the step of:

after performing said step of extending said length of graft tubing, securing each end of said length of graft tubing to a respective one of said first and second tubular body organ sections so that said length of graft tubing opens into both of said first and second tubular body organ sections.

32. The method defined in claim 27 further comprising the step of:

after performing said step of extending said length of graft tubing, longitudinally withdrawing from the patient any of said first and second structures that remain in the patient.

33. The method defined in claim 32 further comprising the step of:

after performing said longitudinally withdrawing step, removing said first and second instruments from the patient.

34. The method defined in claim 27 further comprising the step of:

removing from the patient body organ tubing for use in said length of graft tubing.

35. The method defined in claim 27 wherein said length of graft tubing comprises an artificial graft.

36. The method defined in claim 35 further comprising the step of:

disposing natural body organ tubing coaxially inside of said artificial graft.

37. The method defined in claim 36 wherein said step of extending a length of graft tubing comprises the steps of:

extending said artificial graft along at least one of said first and second structures so that said artificial graft extends between said first and second body organ sections outside of said first and second body organ sections; and extending said natural body organ tubing along at least one of said first and second structures so that said natural body organ tubing extends between said first and second body organ sections inside of said artificial graft.

38. The method defined in claim 35 further comp rising the step of:

after performing said step of extending said artificial graft, securing each end of said artificial graft to a respective one of said first and second tubular stody organ sections so that said artificial graft opens into both of said first and second tubular body organ sections.

39. The method defined in claim 38 further comprising the step of:

after performing said step of extending said natural body organ tubing, securing each end of said natural body organ tubing to a respective one of said first and second tubular body organ sections so that said natural body organ tubing opens into both of said first and second tubular body organ sections.

40. The method defined in claim 27 wherein the distal portion of one of said first and second structures has a selectively closable snare for engaging the distal portion of the other of said first and second structures when the snare is closed on the distal portion of said other structure, and wherein said interengaging step comprises the steps of:

positioning the distal portions of said first and second structures relative to one another so that said snare can engage the distal portion of said other structure; and closing said snare.

* * * * *